(12) United States Patent
Huck et al.

(10) Patent No.: US 8,853,391 B2
(45) Date of Patent: Oct. 7, 2014

(54) TRICYCLIC AZAINDOLES

(75) Inventors: Bayard R. Huck, Sudbury, MA (US); Amanda E. Sutton, Hingham, MA (US); Benny C. Askew, Jr., Marshfield, MA (US); Christopher Charles Victor Jones, Arlington, MA (US); Garry R. Smith, Royersford, PA (US); Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 232 days.

(21) Appl. No.: 13/140,357

(22) PCT Filed: Dec. 3, 2009

(86) PCT No.: PCT/US2009/066534
§ 371 (c)(1),
(2), (4) Date: Aug. 2, 2011

(87) PCT Pub. No.: WO2010/080253
PCT Pub. Date: Jul. 15, 2010

(65) Prior Publication Data
US 2012/0022060 A1  Jan. 26, 2012

Related U.S. Application Data

(60) Provisional application No. 61/203,022, filed on Dec. 18, 2008.

(51) Int. Cl.
C07D 401/14 (2006.01)
C07D 413/14 (2006.01)
C07D 471/14 (2006.01)
C07D 471/04 (2006.01)

(52) U.S. Cl.
CPC .................................. *C07D 471/04* (2013.01)
USPC .............................. 544/126; 544/361; 546/82

(58) Field of Classification Search
None
See application file for complete search history.

(56) References Cited

U.S. PATENT DOCUMENTS

| 3,560,361 | A | * | 2/1971 | Clark et al. | ............... 204/157.72 |
| 6,423,753 | B1 | | 7/2002 | Dougherty | |
| 2009/0012077 | A1 | * | 1/2009 | Dossetter et al. | .......... 514/232.8 |
| 2009/0239854 | A1 | * | 9/2009 | Hung et al. | ................ 514/228.5 |

FOREIGN PATENT DOCUMENTS

| WO | 9722596 A1 | 6/1997 |
|---|---|---|
| WO | 9730035 A1 | 8/1997 |
| WO | 9732856 A1 | 9/1997 |
| WO | 9813354 A1 | 4/1998 |
| WO | 9902166 A1 | 1/1999 |
| WO | 0040529 A1 | 7/2000 |
| WO | 0041669 A2 | 7/2000 |
| WO | 0192224 A1 | 12/2001 |
| WO | 0204434 A1 | 1/2002 |
| WO | 0208213 A1 | 1/2002 |
| WO | 2008016184 A1 | 2/2008 |
| WO | 2009001129 A1 | 12/2008 |
| WO | 2009055828 A1 | 4/2009 |

OTHER PUBLICATIONS

Lucking, et al., ChemMedChem, (2007) 2, 63-77.
Nicolaou, et al., Angewandte Chemie International Edition (2005), 44, 4490-4527.
Dhanabal, et al., Cancer Res. (1999), 59:189-197.
Xin, et al., J. Biol. Chem. (1999), 274:9116-9121.
Praveen, Tyle, Pharmaceutical Research (1986), 3(6):318-326.
Johnson, F. M., et al., Clin. Cancer Res. (2005), 11(19): 6924-6932.
Serrels, A., et al., Mol. Cancer Ther. (2006), 5(12): 3014-3022.
Garcia, R. et al., Oncogene (2001), 20: 2499-2513.
Mukhopadhyay, D., et al., Nature (1995), 375: 557-581.
Ausprunk, et al., Dev. Biol. (1974), 38:237-248.
Berge et al, J. Pharma. Science (1977), 66:1-19.
Gimbrone, et al., J. Natl. Cancer Inst. (1974), 52:413-427.
Nicosia, et al., In Vitro (1982), 18:538549.
Sheu, et al., Anticancer Res. (1998) 18:4435-4441.

\* cited by examiner

*Primary Examiner* — Janet L Andres
*Assistant Examiner* — Timothy R Rozof
(74) *Attorney, Agent, or Firm* — EMD Serono Research Institute; Thomas W. Brown

(57) ABSTRACT

Disclosed are dipyridyl-pyrrole derivative compounds and analogs thereof, pharmaceutical compositions comprising such compounds and processes for preparing the same. The compounds are useful in the treatment of diseases amenable to protein kinase signal transduction inhibition, regulation and/or modulation.

6 Claims, No Drawings

TRICYCLIC AZAINDOLES

FIELD OF THE INVENTION

The present invention relates to protein kinase inhibitors, pharmaceutical compositions comprising such inhibitors, and methods of use thereof.

BACKGROUND OF THE INVENTION

Protein kinases represent a large family of proteins, which play a central role in the regulation of a wide variety of cellular processes, thus maintaining control over cellular function. A partial list of such kinases includes Akt, Axl, Aurora A, Aurora B, Lck, Fyn, Lyn, Yes, dyrk2, epha2, fgfr3, flt-3, vegfr3, igf1r, IKK2, JNK3, Vegfr2, MEK1, MET, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt3, Flt1, PDK1 and Erk.

Abnormal cellular responses triggered by protein kinase-mediated events produce a variety of diseases. These include autoimmune diseases, inflammatory diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Small molecule inhibitors of protein kinases like the Src kinases have been reported recently, but their effect on cytokinesis has yet to be investigated in detail.

The role of Src tyrosine kinase and its inhibitors has been reported in the literature. For example, Garcia et al. described activation of the Stat3 kinase by Src and JAK kinases in promoting growth regulation of human breast carcinoma cells (*Oncogene*, (2001), 20:2499-2513. Mukhopadhyay et al. showed hypoxic induction of human vascular endothelial growth factor expression through activation of c-Src (*Nature* [London], (1995), 375:577-581).

Bristol Myers Squibb described their drug, dasatinib, as a tyrosine kinase inhibitor that suppresses invasion and induces cell cycle arrest and apoptosis in squamous cell carcinoma and non-small cell lung cancer cells (*Clin. Cancer Res.*, (2005), 11(19):6924-6932).

Serrels et al. disclosed the identification of potential biomarkers for measuring inhibition of Src activity in colon cancer cells with dasatinib (*Mol. Cancer. Ther.*, (2006), 5(12):3014-3022). PP Takeda Pharmaceuticals Co., Ltd., disclosed pyrido-indole derivatives that are inhibitors of tyrosine kinases and cyclin-dependent kinases, and so are useful as antitumor, antibacterial and anti-viral agents (WO 2008/016184).

However, the need exists for a protein kinase inhibitor that is capable of inhibiting, modulating and/or regulating signal transduction by aberrant protein kinases, thereby effectively treating proliferative diseases such as cancers and cardiovascular, neurodegenerative, inflammatory, and endocrine-related diseases. It is also desirable for this protein kinase inhibitor to be useful in combination therapies for disease treatment and as a diagnostic tool.

These compounds of the present invention and pharmaceutical compositions comprising them are presented either individually or in kit form. Included in this invention also are processes for preparing the compounds that actively modulate or inhibit unregulated protein kinase activity.

Additional objects, features and advantages of the present invention will become apparent to those skilled in the art from the following description and claims.

SUMMARY OF THE INVENTION

The compounds of the invention are selective and highly potent adenosine triphosphate (ATP) competitive inhibitors of Src tyrosine kinases. kinase. The present invention also provides pharmaceutically acceptable derivatives, solvates, salts, tautomers and stereoisomers of these compounds, including mixtures thereof in all ratios. Diseases treated by the use of these novel compounds include primary, secondary, and metastatic cancers such as melanoma, lymphoma, leukemia, colon, colorectal, breast, lung, kidney, pancreatic, renal, CNS, stomach, ovarian, prostate and cervical cancers. Moreover, allergies, asthma, neurodegenerative, endocrine, immunologic, cardiovascular, metabolic, and proliferative diseases all may be treated by use of the compounds of the invention.

In one aspect the invention provides compounds according to Formula I:

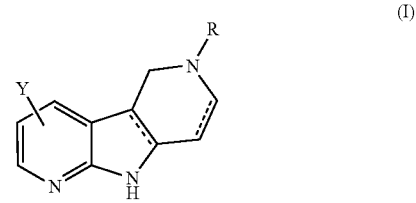

(I)

wherein

R is H; halo; CN; $NO_2$; $C_1$-$C_6$ alkyl; $CF_3$; aryl; heteroaryl; aralkyl; alkaryl; heteroalkyl; carbocycle; C(=O)OR'; alkyl-C(=O)—; —C(=O)aryl; —C(=O)heteroaryl; —C(=O)NH-aryl; —C(=O)NH-heteroaryl; aryl-C(=O)—; heteroaryl-C(=O); OR'; R'—$SO_2$—; $SO_2$—R'; SR'; R'—NH—C(=O)—; alkyl-O—C(=O)—; R'-alkyl-; R'—C(=O); or NR'R';

R' is H; O; S; $CONH_2$; alkyl; haloalkyl; alkylhalo; haloaryl; haloheteroaryl; carbocycle; aryl; heteroaryl; or heteroalkyl;

Y is H; halo; aryl; heteroaryl; NH-heteroaryl; NH-aryl; -aryl-C(=O)—NH—NH-aryl; aryl-C(=O)—NH—; -heteroaryl-C(=O)NH; -heteroaryl-C(=O)—NH—NH-aryl; -heteroaryl-C(=O)NH—NH-heteroaryl; -aryl-C(=O)—NH—NH-heteroaryl; -aryl-C(=O)—NH—; -heteroaryl-C(=O)NH; aryl-alkyl-NH—; heteroaryl-alkyl-NH; aryl-C(=O)—NH-aryl-NH—; heteroaryl-C(=O)—NH-aryl-NH; heteroaryl-C(=O)—NH-heteroaryl-NH; aryl-C(=O)—NH-heteroaryl-NH; alkyl-NH—$SO_2$—; R'—NH—; R'—O—R'—NH—; NR'R'-alkyl-; or R'-alkyl-;

-------- denotes the presence or absence of a double bond;

aryl, heteroaryl or carbocycle optionally may be substituted or unsubstituted, and may be a mono-, bi- or tricyclic ring structure in any combination of aryl, heteroaryl, and/or carbocyclic rings; and a pharmaceutically acceptable prodrug, derivative, solvate, salt, tautomer and stereoisomer thereof, including mixtures thereof in all ratios.

Examples of preferred embodiments include the following:

In a first preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

In a second preferred embodiment of the present invention, R is ethanone, and Y is an benzamidophenyl amino moiety.

In a third preferred embodiment, R is ethanone, and Y is phenylamino.

In a first subembodiment of the third preferred embodiment, Y is phenyl amino and R is 3-chlorophenylmethanone.

In a fourth preferred embodiment of the invention, R is 3-chloro-benzenesulfonyl and Y is phenylamino.

Also encompassed by the present invention are methods of treating a subject in need of inhibiting a kinase protein comprising administering to the subject an effective amount of a kinase inhibitor according to Formula I.

In a preferred embodiment, the compound according to Formula I is incorporated into a pharmaceutical formulation along with one or more pharmaceutically acceptable diluent, excipient, or carrier, and which further optionally may be packaged as a kit. Provided herein are such pharmaceutical compositions and methods of modulating and/or inhibiting unregulated or disturbed protein kinase activity in order to treat or cure proliferative diseases, including all types of cancers, comprising administering to a subject in need thereof an effective amount of a kinase inhibitor according to Formula I. In a further aspect the invention provides a method for treating or preventing a disease or condition that is a member selected from tumor formation, angiogenesis, arteriosclerosis, ocular diseases, inflammatory diseases, arthritis, and restinosis, among others. The method includes administering to a subject in need thereof a therapeutically effective amount of a compound of Formula I or a pharmaceutically acceptable salt, prodrug, enantiomer, tautomer, hydrate, solvate or racemic mixture thereof. The compounds of Formula I furthermore can be used to provide additive or synergistic effects in certain existing cancer chemotherapies, and/or can be used to restore the efficacy of certain existing cancer chemotherapies and radiotherapies.

Also included within the scope of the invention are compounds 1-78, and a pharmaceutically acceptable salt, prodrug, hydrate, solvate, tautomer, enantiomer or racemic mix of each thereof.

As used herein, the term "solvate" of a compound is meant to comprise solvate of a salt of a compound.

Additional embodiments of the present invention include: a compound according to Formula I for use as a medicament; use of the compound according to Formula I for the preparation of a medicament for the treatment of a subject in need of inhibiting a kinase protein; and use of the compound according to Formula I for the preparation of a medicament for the suppression or reduction of cellular proliferation in single-site or metastatic cancers, or for the inhibition or suppression of cancer metastases.

The present invention also encompasses a compound according to Formula I, or a pharmaceutically acceptable derivative, solvate, salt, tautomer and stereoisomer thereof, including mixtures thereof in all ratios, for use in therapy, such as treating a subject in need of modulating or inhibiting a kinase protein, wherein the subject has a proliferative or an inflammatory disease.

Methods of synthesizing the compounds of the present invention also are encompassed within the present invention.

Moreover, the present invention is related to the combined use of a compound of Formula I together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

BRIEF DESCRIPTION OF THE DRAWINGS

None.

DETAILED DESCRIPTION OF THE INVENTION

The present invention relates to compounds that inhibit, regulate and/or modulate signal transduction by protein kinases, and by Src kinases in particular. The invention also relates to pharmaceutical compositions that comprise these compounds, and to methods for using the compounds in the treatment of kinase-related diseases and complaints. In a first aspect, the present invention provides a compound having a structure according to Formula I:

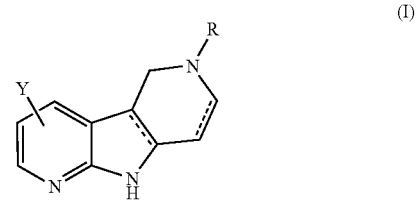

(I)

wherein

R is H; halo; CN; NO$_2$; C$_1$-C$_6$ alkyl; CF$_3$; aryl; heteroaryl; aralkyl; alkaryl; heteroalkyl; carbocycle; C(=O)OR'; alkyl-C(=O)—; —C(=O)aryl; —C(=O)heteroaryl; —C(=O)NH-aryl; —C(=O)NH-heteroaryl; aryl-C(=O)—; heteroaryl-C(=O); OR'; R'—SO$_2$—; SO$_2$—R'; SR'; R'—NH—C(=O)—; alkyl-O—C(=O)—; R'-alkyl-; R'—C(=O); or NR'R'; aryl-C(=O); aryl-NH—C(=O)—; aryl-C(=O)—; OR'; R'—SO$_2$—; SO$_2$—R'; SR'; R'—NH—C(=O)—; alkyl-O—C(=O)—; R'-alkyl-; R'—C(=O); or NR'R';

R' is H; O; S; alkyl; haloalkyl; alkylhalohaloaryl; haloheteroaryl; carbocycle; aryl; heteroaryl; or heteroalkyl;

Y is H; halo; aryl; heteroaryl; aryl-NH; NH-heteroaryl; NH-aryl; aryl-C(=O)—NH—NH-aryl; aryl-C(=O)—NH—; -heteroaryl-C(=O)NH; -heteroaryl-C(=O)—NH—NH-aryl; -heteroaryl-C(=O)NH—NH-heteroaryl; -aryl-C(=O)—NH—NH-heteroaryl; -aryl-C(=O)—NH—; -heteroaryl-C(=O)NH; aryl-alkyl-NH—; heteroaryl-alkyl-NH; aryl-C(=O)—NH-aryl-NH—; heteroaryl-C(=O)—NH-aryl-NH; heteroaryl-C(=O)—NH-heteroaryl-NH; aryl-C(=O)—NH-heteroaryl-NH; alkyl-NH—SO$_2$—; R'—NH—; R'—O—R'—NH—; NR'R'-alkyl-; or R'-alkyl-;

-------- denotes the presence or absence of a double bond;

aryl, heteroaryl or carbocycle optionally may be substituted or unsubstituted, and may be a mono-, bi- or tricyclic ring structure in any combination of aryl, heteroaryl, and/or carbocyclic rings; and a pharmaceutically acceptable prodrug, derivative, solvate, salt, tautomer and stereoisomer thereof, including mixtures thereof in all ratios.

In a preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

The compounds of the present invention are useful for the treatment of a subject in need of inhibition or modulation of a protein kinase, and so are useful in the treatment of inflammatory and/or proliferative disorders.

In a second preferred embodiment of the present invention, R is ethanone, and Y is a benzamidophenyl amino moiety.

In a third preferred embodiment, R is ethanone, and Y is phenylamino.

In a first subembodiment of the third preferred embodiment, R is 3-chlorophenylmethanone and Y is phenyl amino.

In a second subembodiment of the third preferred embodiment, R is 3-chloro-phenyl-amino-methanone and Y is phenyl amino.

In a fourth preferred embodiment of the invention, R is 3-chloro-benzenesulfonyl and Y is phenylamino.

In a fifth preferred embodiment of the invention, R is 3-chloro-benzoyl and Y is amino phenyl benzamide.

In a sixth preferred embodiment of the invention, R is ethanone and Y is benzenesulfonamide.

In a seventh preferred embodiment of the invention, R is methanone and Y is 5-chloro-benzo[1,3]dioxol-4-ylamino.

In a first preferred subembodiment of the seventh preferred embodiment invention, R is cyclopropyl methanone and Y is 5-chloro-benzo[1,3]-dioxol-4-ylamino.

In a second preferred subembodiment of the seventh preferred embodiment of the invention, R is cyclobutyl methanone and Y is 5-chloro-benzo[1,3]-dioxol-4-ylamino.

In a third preferred subembodiment of the seventh preferred embodiment of the invention, R is cyclopentyl methanone and Y is 5-chloro-benzo[1,3]-dioxol-4-ylamino.

In a fourth preferred subembodiment of the seventh preferred embodiment of the invention, R is cyclohexyl methanone and Y is 5-chloro-benzo[1,3]-dioxol-4-ylamino.

In a fifth preferred subembodiment of the seventh preferred embodiment of the invention, R is 2-methyl-propan-1-one and Y is 5-chloro-benzo[1,3]-dioxol-4-ylamino.

In a further preferred embodiment the present invention relates to medicaments comprising at least one compound of the Formula I, and at least one further medicament active ingredient.

Preferably such medicaments are for the treatment of diseases which are influenced by inhibition of an enzyme that is a Src tyrosine kinase.

A very preferred medicament according to the invention is for the treatment of diseases which are influenced by modulation or inhibition of Src kinase.

In a further preferred embodiment the present invention relates to a kit or set comprising separate packs of (a) an effective amount of a compound of the Formula I according to the invention, and (b) an effective amount of a further medicament active ingredient.

The compounds of the present invention are useful for the treatment of a subject in need of inhibition or modulation of a protein kinase, and so are useful in the treatment of inflammatory and/or proliferative disorders such as cancers. Thus, also encompassed by the present invention are methods of treating a subject in need of modulating or inhibiting a kinase protein comprising administering to the subject an effective amount of a kinase inhibitor according to Formula I. The compounds of Formula I furthermore can be used to provide additive or synergistic effects in existing cancer chemotherapies, and/or can be used to restore the efficacy of existing cancer chemotherapies and radiotherapies.

In a preferred embodiment, the compound according to Formula I is incorporated into a pharmaceutical formulation along with one or more of a pharmaceutically acceptable diluent, excipient, or carrier, and further optionally may be packaged as a kit.

In a further aspect the invention provides a method for treating or preventing a disease or condition that is a member selected from tumor formation, angiogenesis, arteriosclerosis, ocular diseases, inflammatory diseases, arthritis, and restinosis, among others. The method includes administering to a subject in need thereof a therapeutically effective amount of a compound of Formula I or a pharmaceutically acceptable salt, prodrug, enantiomer, tautomer, hydrate, solvate or racemic mixture thereof.

Also included within the scope of the invention are compounds 1-78, and a pharmaceutically acceptable salt, prodrug, hydrate, solvate, tautomer, enantiomer or racemic mix of each thereof.

Additional embodiments of the present invention include: a compound according to Formula I for use as a medicament; use of the compound according to Formula I for the preparation of a medicament for the treatment of a subject in need of inhibiting a kinase protein; and use of the compound according to Formula I for the preparation of a medicament for the suppression or reduction of cellular proliferation in single-site or metastatic cancers, or for the inhibition or suppression of cancer metastases.

The present invention also is related to the combined use of a compound of Formula I together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory and hematological diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

II. DEFINITIONS

As used herein, a description of the compounds of the invention in every case includes a pharmaceutically acceptable salt, solvate, hydrate, prodrug, tautomer, enantiomer, stereoisomer, analog or derivative thereof, including mixtures thereof in any ratios.

Where substituent groups are specified by their conventional chemical formulae, written from left to right, they optionally encompass substituents resulting from writing the structure from right to left, e.g., —CH$_2$O— optionally also recites —OCH$_2$—.

The term "alkyl", by itself or as part of another substituent, unless otherwise stated means an unbranched (linear) or branched chain, or a cyclic hydrocarbon radical, or combination thereof, having 1, 2, 3, 4, 5, 6, 7, 8, 9 or 10 C atoms. The term preferably denotes methyl, ethyl, propyl, isopropyl, butyl, isobutyl, sec-butyl or tert-butyl, pentyl, or hexyl, and includes cycloalkyl and bicycloalkyl, e.g. cyclopropyl, cyclobutyl, cyclopentyl, cyclohexyl, cycloheptyl, norbornene, and the like. One to seven hydrogen atoms in an alkyl chain as defined may be replaced by F, Cl and/or Br, and/or one or two CH2 groups may be replaced by O, S, SO, SO$_2$ and/or CH=CH groups.

The terms "haloalkyl" and "alkylhalo" as used herein, respectively, mean a halogen atom such as chlorine, bromine, iodine or fluorine bound to an alkyl group, and in reverse, an alkyl group bound to a halogen atom.

The term "alkylene" denotes an optionally substituted, unbranched (linear) or branched chain that by itself or as part of another substituent means a divalent radical derived from an alkane, as exemplified by —CH$_2$CH$_2$CH$_2$—. "Alkylene" preferably denotes methylene, ethylene, propylene, isopropylene, butylene, isobutylene, sec-butylene or tert-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, or difluoromethylene. Especially preferred is an alkylene having 1, 2, 3, 4, 5 or 6 C atoms, preferably methylene, ethylene, propylene, isopropylene, butylene, isobutylene, sec-butylene, tert-butylene, pentylene, hexylene, difluoromethylene, tetrafluoroethylene or 1,1-difluoroethylene.

A "cyclic alkylene" ("cycloalkylene") preferably denotes cyclopropylene, cyclobutylene, cyclopentylene, cyclohexylene or cycloheptylene.

The term "aryl" means, unless otherwise stated, means a polyunsaturated, aromatic, single ring or multiple rings, preferably from 1 to 3 rings, the latter of which are fused together or linked covalently. The term "aryl" denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino) phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl including difluorophenyl, o-, m- or p-bromophenyl including dibromophenyl, o-, m- or p-chlorophenyl including dichlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl) phenyl, o-, m- or p-[2-(morpholin-4-yl)ethoxy]phenyl, o-, m- or p-[3-(N,N-diethylamino)propoxy]phenyl, o-, m- or p-[3-(3-diethylamino-propyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N, N-dimethylamino- or 3-nitro-4-N,N-dimethyl-aminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 2-chloro-4-fluoro, 5-chloro-benzo[1,3]-dioxole, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-6-acetamidophenyl, 3-fluoro-4-methoxyphenyl, 3-amino-6-methylphenyl, 3-chloro-4-acetamidophenyl or 2,5-dimethyl-4-chlorophenyl In a preferred embodiment, "aryl" preferably denotes a phenyl that is unsubstituted or mono-, di- or trisubstituted independently by one or more halogens, OR, CN, CONH$_2$, CONH-alkyl or a heterocycle, where R is H, alkyl or alkyl chain comprising one or more heteroatoms; or where the substituents join with the carbon atoms of the phenyl to which they are bound to form a second ring, thereby providing a bicyclic structure.

The term "heteroaryl" refers to an aryl ring that contains from one to four heteroatoms selected from N, O, S, Si, P and B, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 7-azaindole, 1-isoquinolyl, 5-isoquinolyl, 2-quinoxalinyl, 5-quinoxalinyl, 3-quinolyl, 6-quinolyl, 1-piperidinyl, 3-benzofuranyl, and 4-benzodioxinyl. Substituents for each of the above noted aryl and heteroaryl ring systems are selected from the group of acceptable substituents described below.

For brevity, the term "aryl" when used in combination with other terms, such as for example, aryloxy, arylthioxy, or arylalkyl, optionally includes both aryl and heteroaryl rings as defined above. Thus, the term "arylalkyl" or "aralkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). This same definition is true in reverse for the term "alkaryl", which includes radicals in which an alkyl group is attached to an aryl group. Each of the terms "alkyl," "heteroalkyl," "aryl" and "heteroaryl" optionally include unsubstituted, mono-, di- or tri-unsubstituted forms of the indicated radical.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Substituents for the alkyl and heteroalkyl radicals, including those groups often referred to as alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, and —R$_1$, wherein R$_1$ is —OH, O-alkyl, —CN, -halo, —C(O)OH, —C(O)O(alkyl), —C(O)NH$_2$, —C(O)NH (alkyl), —C(O)N(alkyl)$_2$, —CH$_2$OH, —CH$_2$O(alkyl), —CH$_2$NH$_2$, —CH$_2$NH(alkyl), —CH$_2$N(alkyl)$_2$, —SO$_2$OH, —SO$_2$O(alkyl), —SO$_2$NH$_2$, —SO$_2$NH(alkyl), and —SO$_2$N (alkyl)$_2$. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OH, —O-alkyl, —CN, -halo, —C(O)OH, —C(O)O(alkyl), —C(O)NH$_2$, —C(O)NH(alkyl), —C(O)N(alkyl)$_2$, —CH$_2$OH, —CH$_2$O(alkyl), —CH$_2$NH$_2$, —CH$_2$NH(alkyl), —CH$_2$N(alkyl)$_2$, —SO$_2$OH, —SO$_2$O(alkyl), —SO$_2$NH$_2$, —SO$_2$NH(alkyl), N(alkyl)SO$_2$(alkyl), and —SO$_2$N(alkyl)$_2$.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes, norbornanes, and the like.

The term "treatment" as used herein refers both to prevention of a particular disease or treatment of a pre-existing condition.

The phrase "therapeutically effective amount" as used herein means that amount of a compound, material, or composition comprising a compound of the present invention which is effective for producing some desired therapeutic effect by simultaneous blocking or inhibiting of protein kinase receptors in a mammal, thereby blocking the biological consequences of that pathway in the treated cells, at a reasonable benefit/risk ratio applicable to any medical treatment.

The term "pharmaceutically acceptable salts" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *J. Pharma. Science* 1977, 66: 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N methylglutamine. The aluminium salts of the compounds of the Formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the Formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2 hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2 naphthalenesulfonate, nicotinate, nitrate, oxalate, oleate, palmoate, pectinate, persulfate, phenylacetate, 3 phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the Formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as (C1-C4)alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, dodecyl, lauryl, myristyl and stearyl chloride, bromide and iodide; and aryl(C1-C4)alkyl halides, for example benzyl chloride and phenethyl bromide. Both water- and oil-soluble compounds according to the invention can be prepared using such salts.

The above-mentioned pharmaceutical salts that are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the Formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As stated, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group that is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

The term "pharmaceutically acceptable salt" as contained herein means an active ingredient which comprises a compound of the Formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the Formula I and/or pharmaceutically usable derivatives, solvates and stereoisomers thereof, including mixtures thereof in all ratios, and optionally excipients and/or adjuvants.

As used herein, the term "prodrug" means a form of the compound that readily undergoes one or more chemical changes under physiological conditions to provide an active form of the compound of the present invention. For instance, typical prodrugs include carboxylic acid ester forms of the compounds of the invention. In an exemplary embodiment, the prodrug is suitable for treatment/prevention of those diseases and conditions that require the drug molecule to cross the blood brain or other membrane bather. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention exist in "unsolvated" forms as well as "solvated" forms, including "hydrated" forms. In general, the solvated forms are equivalent to unsolvated forms, and both are encompassed within the scope of the present invention. Certain compounds of the present invention may exist in multiple crystalline or amorphous forms. In general, all physical forms may be used in the methods contemplated herein and are intended to be within the scope of the present invention. The phrase "a compound or a pharmaceutically acceptable salt, hydrate, polymorph or solvate of a compound" is meant to include both a material that exists in one or more than one of these states.

As used herein, the term "heteroatom" includes oxygen (O), nitrogen (N), sulfur (S), silicon (Si), boron (B), and phosphorus (P).

The term "heteroalkyl," by itself or in combination with another term, unless otherwise stated, means a stable straight or branched chain, cyclic hydrocarbon radical, or combinations thereof, consisting of the stated number of carbon atoms and at least one heteroatom selected from the group consisting of O, N, Si, B, P, and S, wherein the nitrogen and sulfur atoms may optionally be oxidized and the nitrogen heteroatom may optionally be quaternized. The heteroatom(s) O, N, S, B, P, and Si may be placed at any interior position of the heteroalkyl group or at the position at which the alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group for alkylene and heteroalkylene is implied by the direction in which the formula of the linking group is written. For example, the formula —CO$_2$R'— represents both —C(O)OR' and —OC(O)R'.

The terms "cycloalkyl" or "carbocycle" and "heterocycloalkyl", by themselves or in combination with other terms, unless otherwise stated, mean cyclic versions of "alkyl" and "heteroalkyl", respectively. Additionally, for heterocycloalkyl, a heteroatom occupies any position in the cycle. A "cycloalkyl", "carbocycle" or "heterocycloalkyl" substituent may be attached to the remainder of the molecule directly or through a linker, wherein the linker is, for example, alkyl. Examples of cycloalkyl include, but are not limited to, cyclopentyl, cyclohexyl, 1-cyclohexenyl, 3-cyclohexenyl, cycloheptyl, norbornanyl, norbornene, and the like. The term "carbocycle" as used herein refers to any fully saturated ring structure, including without limitation, cyclopropyl, cyclobutyl, cyclopentyl, cyclohexyl, cycloheptyl, and the like, and also includes mono-, bi- and tri-cyclic forms of the same. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Unless otherwise stated, the terms "halo" or "halogen," by themselves or as part of another substituent, mean a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, difluoromethyl, fluoromethyl, 2,2,2-trifluoroethyl, 4-chlorobutyl, 3-bromopropyl, and the like.

As used herein, the term "tricyclic azaindole" means a scaffold depicted by the following structural arrangement:

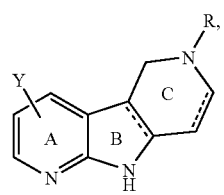

wherein the A and C rings optionally may be substituted.

Reagents utilized in the syntheses contained herein, unless otherwise noted, have the following meanings: "S-Phos" is 2-dicyclohexylphosphino-2',6'-dimethoxybiphenyl; "Pd(OAc)$_2$" is palladium(II) acetate; "K$_2$CO$_3$" is potassium carbonate; "KOH" is potassium hydroxide; "X-Phos" is 2-dicyclohexylphosphino-2',4',6'-triisopropylbiphenyl; "NaOtBu" is sodium tert-butoxide; "DIEA" is N,N-diisopropylethylamine and "t-BuOH" is tertiary-butyl hydroxide.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The term "host 'or "patient in need thereof" as used herein may be any mammalian species, for example a primate species, particularly humans; rodents; rabbits; horses, cows, sheep, dogs, cats, etc. Animal models are of interest for veterinary treatment and for experimental investigations, providing a model for treatment of human disease.

By "therapeutically effective amount" of a compound means the amount of the compound that, upon administration, provides the desired beneficial result in a host or patient in need thereof. This amount depends on a number of factors, including, for example, the age and weight of the host, the precise condition that requires treatment and its severity, the nature of the formulation, and the method of administration, and is ultimately determined by the a physician or veterinarian. An effective amount of a compound according to the invention for the treatment of neoplastic growth, for example, is generally in the range from 0.1 to 100 mg/kg/day of body weight of the host recipient. More particularly it is in the range from 1 to 10 mg/kg/day of body weight. Thus, the actual amount per day for an adult mammal weighing 70 kg is usually between 70 and 700 mg, where this amount can be administered as a single dose per day, or may also be administered in a series of partial doses such as, for example, two, three, four, five or six per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

Any drug dosage depends upon the specific compound active agent, the specific disease, patient status, etc. A therapeutic dose typically is considered sufficient at the level at which it reduces the undesired cell population in the target tissue while the viability of the patient is maintained. The treatment is generally continued until a reduction in cell population has occurred, for example, minimally about 50% reduction in cell burden, and may be continued until essentially no more undesired cells are detected in the body.

III. PHARMACEUTICAL COMPOSITIONS, DOSAGES AND ROUTES OF ADMINISTRATION

While compounds of the present invention can be administered as the raw chemical, it is preferable to present them as a pharmaceutical composition. Thus, one aspect of the present invention provides a pharmaceutical composition comprising a compound of Formula I or a pharmaceutically acceptable salt, hydrate or solvate thereof, together with one or more pharmaceutically acceptable carriers and optionally one or more other therapeutic ingredients. The carrier(s) are "acceptable" in the sense of being compatible with the other ingredients of the formulation and not deleterious to the recipient thereof. The term "pharmaceutically acceptable carrier" includes vehicles, diluents, excipients and other elements appropriate for incorporation into a pharmaceutical formulation.

Pharmaceutical compositions containing compounds of Formula I may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 0.1 mg per day to about 7000 mg per day, preferably about 1 mg per day to about 100 mg per day, and more preferably, about 25 mg per day to about 50 mg per day, in single or divided doses. Preferred dosage unit formulations are those that comprise a daily dose or partial dose, as indicated above, or a corresponding fraction thereof of an active ingredient. Furthermore, pharmaceutical formulations of this type can be prepared using a process that is generally known in the pharmaceutical art. In some embodiments, the total daily dose may range from about 50 mg to about 500 mg per day, and preferably, about 100 mg to about 500 mg per day. Normally it is recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions. The active ingredient also may be present as a bolus, electuary or paste.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate like starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser like agar-agar, calcium carbonate or sodium carbonate, may likewise be added in order to improve the availability of the medicament after the capsule has been taken.

In addition, if desired or necessary, suitable binders, lubricants and disintegrants as well as dyes can be incorporated into the mixture. Suitable binders include starch, gelatin, natural sugars, such as, for example, glucose or beta-lactose, sweeteners made from maize, natural and synthetic rubber like acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted hereto, starch, methylcellulose, agar, bentonite, xanthan gum and the like. Tablets are formulated by preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base as described above, and optionally with a binder, such as carboxymethylcellulose, an alginate, gelatine or polyvinylpyrrolidone, a dissolution retardant, such as, for example, paraffin, an absorption accelerator, such as a quaternary salt, and/or an absorbent like bentonite, kaolin or dicalcium phosphate. The powder mixture can be granulated by wetting it with a binder, such as a syrup, starch paste, acadia mucilage or solutions of cellulose or polymer materials, and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting molds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac-sealing layer, a layer of sugar or polymer material, and a gloss layer of wax may be present. Dyes can be added to these coatings in order to be able to differentiate between different dosage units.

Oral liquids, such as solutions, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of a compound of Formula I in a non-toxic vehicle. Solubilisers and emulsifiers like ethoxylated isostearyl alcohols and polyoxyethylene sorbitol ethers, preservatives, flavor additives, such as peppermint oil, natural sweeteners or saccharin, or other artificial sweeteners and the like, also can be added.

The unit dosage formulations for oral administration, if desired, can be encapsulated in microcapsules. The formulation can also be prepared in such a way that the release is extended or retarded, such as, for example, by coating or embedding of particulate material in polymers, wax and the like.

The compounds of Formula I and salts, solvates and physiologically functional derivatives thereof can also be administered in the form of liposome delivery systems, like small or large unilamellar or multilamellar vesicles, large unilamellar vesicles and multilamellar vesicles. Liposomes can be formed from various phospholipids, such as cholesterol, stearylamine or phosphatidylcholines.

The compounds of Formula I and salts, solvates and physiologically functional derivatives thereof also can be delivered using monoclonal antibodies as individual carriers to which the compound molecules are coupled. The compounds further may be coupled to soluble polymers as targeted medicament carriers. Such polymers encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, (1986) 3(6):318.

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of a formulation to give an ointment, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered by rapid inhalation via the nasal passages from a container containing the powder held close to the nose. Suitable formulations for administration as nasal spray or nose drops with a liquid as carrier substance encompass solutions of the active-ingredient in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The formulations may also comprise other agents usual in the art with respect to the particular type of formulation. Thus, for example, formulations that are suitable for oral administration may comprise flavors.

A formulation of the compound or composition includes any suitable form for parenteral (subcutaneous, intradermal, intramuscular, intravenous, peritoneal and intraarticular), rectal, ionotophoretic, intranasal, inhalation, and oral (including dermal, buccal, sublingual and intraocular) administration. The most suitable route will depend upon the condition and disorder of the recipient. All methods include the step of bringing into association a compound or a pharmaceutically acceptable salt or solvate thereof ("active ingredient") with the pharmaceutically acceptable carrier that constitutes one or more accessory ingredients. In general, the formulations are prepared by uniformly and intimately bringing into association the active ingredient with liquid carriers or finely divided solid carriers or both, and then, if necessary, shaping this formulation into the desired product shape. Oral formulations are well known to those skilled in the art, and general methods for preparing them are found in any standard pharmacy textbook, for example, Remington: *The Science and Practice of Pharmacy*., A. R. Gennaro, ed. (1995), Lippincott.

One aspect of the present invention contemplates the treatment of the disease/condition with the pharmaceutically active agent that may be sold in kit form. The kit comprises a compound of the present invention contained within a syringe, box, bag, and the like. Typically, the kit comprises directions for the administration of the compound. The kit form is particularly advantageous when different dosage concentrations and/or forms (e.g., oral and parenteral) are sold, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). They generally consist of a sheet of relatively stiff material covered with a foil of a preferably transparent plastic material. During the packaging process recesses are formed in the plastic foil. The recesses have the size and shape of the tablets or capsules to be packed. The tablets or capsules are placed in the recesses and the sheet of relatively stiff material is sealed against the plastic foil at the face of the foil which is opposite from the direction in which the recesses were formed. Particular dosage information normally is stamped onto each blister pack.

In another specific embodiment of the invention, a dispenser designed to dispense the daily doses one at a time in the order of their intended use is provided.

IV. METHODS OF TREATMENT OR PREVENTION

In a further aspect the invention provides a method for treating or preventing a disease or condition that is a member selected from kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, haematological diseases, cirrhosis, diabetes and vascular and immune diseases in mammals. The method includes administering to a subject in need thereof a therapeutically effective amount of a compound of Formula I or a pharmaceutically acceptable salt, hydrate, prodrug, tautomer, enantiomer, or racemic mix thereof:

Subjects for treatment according to the present invention include humans (patients) and other mammals in need of therapy for the stated condition.

Compounds of the invention possess unique pharmacological characteristics with respect to inhibition of cellular division and influence the activity of the Src kinase enzymes in cells. Therefore, these compounds are effective in treating conditions and disorders, especially cancer-related tumors and disorders, which are modulated by Src kinase activity. In one embodiment, compounds of the invention are associated with diminished side effects compared to other current standards of treatment.

Compounds of the invention are typically more selective than known anti-cancer drugs, and demonstrate higher selectivity for inhibiting certain protein kinase activity. The compounds also exhibit an advantageous profile of activity including good bioavailability. Accordingly, they offer advantages over many art-known methods for treating disorders associated with unregulated or disturbed protein kinase activity.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents, for example, cis-platin, carboplatin, cyclophosphamide, nitrogen mustard, melphalan, chlorambucil, busulphan and nitrosoureas; antimetabolites, for example, antifolates such as fluoropyrimidines like 5-fluorouracil and tegafur, raltitrexed, methotrexate, cytosine arabinoside, hydroxyurea and gemcitabine; antitumour antibiotics, for example, anthracyclines, like adriamycin, bleomycin, doxorubicin, daunomycin, epirubicin, idarubicin, mitomycin-C, dactinomycin and mithramycin; antimitotic agents, for example, vinca alkaloids, like vincristine, vinblastine, vindesine and vinorelbine, and taxoids, like taxol and taxotere; topoisomerase inhibitors, for example, epipodophyllotoxins, like etoposide and teniposide, amsacrine, topotecan, irinotecan and camptothecin; and cell-differentiating agents, for example, all-trans-retinoic acid, 13-cis-retinoic acid and fenretinide;

(ii) cytostatic agents, such as antioestrogens, for example, tamoxifen, toremifene, raloxifene, droloxifene and iodoxyfene, oestrogen receptor downregulators, for example, fulvestrant, antiandrogens, for example, bicalutamide, flutamide, nilutamide and cyproterone acetate, LHRH antagonists or LHRH agonists, for example, goserelin, leuprorelin and buserelin, progesterones, for example, megestrol acetate, aromatase inhibitors, for example, as anastrozole, letrozole, vorazole and exemestane; and inhibitors of 5'-reductase, such as finasteride;

(iii) agents which inhibit cancer cell invasion, for example, metalloproteinase inhibitors, like marimastat, and inhibitors of urokinase plasminogen activator receptor function;

(iv) inhibitors of growth factor function, for example, such inhibitors include growth factor antibodies, growth factor receptor antibodies, for example, the anti-erbb2 antibody trastuzumab [Herceptin™] and the anti-erbb1 antibody cetuximab [C225], farnesyl transferase inhibitors, serine/threonine kinase inhibitors and serine/threonine kinase inhibitors, for example, inhibitors of the epidermal growth factor family, for example, EGFR family serine/threonine kinase inhibitors, such as N (3-chloro-4-fluorophenyl)-7-methoxy-6-(3-morpholinopropoxy) quinazolin-4-amine (gefitinib, AZD1839), N (3-ethynylphenyl)-6,7 bis(2-methoxyethoxy)quinazolin-4-amine (erlotinib, OSI-774) and 6 acrylamido-N-(3-chloro-4-fluorophenyl)-7-(3-morpholinopropoxy)quinazolin-4-amine (CI 1033); inhibitors of the platelet-derived growth factor family; and inhibitors of the hepatocyte growth factor family;

(v) antiangiogenic agents, such as those which inhibit the effects of vascular endothelial growth factor, for example, the anti-vascular endothelial cell growth factor antibody bevacizumab [Avastin™]; compounds such as those disclosed in published international patent applications WO 97/22596, WO 97/30035, WO 97/32856 and WO 98/13354) and compounds that work by other mechanisms, (for example, linomide, inhibitors of integrin function and angiostatin;

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example, those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT; gene-directed enzyme pro-drug therapy approaches, such as those using cytosine deaminase, thymidine kinase or a bacterial nitroreductase enzyme; and approaches for increasing patient tolerance to chemotherapy or radiotherapy, such as multidrug resistance gene therapy; and (ix) immunotherapy approaches, including, for example, ex-vivo and in-vivo approaches for increasing the immunogenicity of patient tumour cells, such as transfection with cytokines like interleukin 2, interleukin 4 or granulocyte-macrophage colony stimulating factor; approaches for decreasing T cell anergy; approaches using transfected immune cells, such as cytokine-transfected dendritic cells; approaches using cytokine-transfected tumour cell lines; and approaches using anti-idiotypic antibodies.

The medicaments from Table 1 below are preferably, but not exclusively, combined with the compounds of the formula I.

TABLE 1

| Alkylating agents | Cyclophosphamide | Lomustine |
|---|---|---|
| | Busulfan | Procarbazine |
| | Ifosfamide | Altretamine |

TABLE 1-continued

| | | |
|---|---|---|
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | |
| | | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | IDN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |

TABLE 1-continued

| | | |
|---|---|---|
| Aromatase inhibitors | Aminoglutethimide<br>Letrozole<br>Anastrazole<br>Formestan | Exemestan<br>Atamestan (BioMedicines)<br>YM-511 (Yamanouchi) |
| Thymidylate synthase inhibitors | Pemetrexed (Eli Lilly)<br>ZD-9331 (BTG) | Nolatrexed (Eximias)<br>CoFactor ™ (BioKeys) |
| DNA antagonists | Trabectedin (PharmaMar)<br>Glufosfamide (Baxter International)<br>Albumin + 32P (Isotope Solutions)<br>Thymectacin (NewBiotics)<br>Edotreotid (Novartis) | Mafosfamide (Baxter International)<br>Apaziquone (Spectrum Pharmaceuticals)<br>O6-Benzylguanine (Paligent) |
| Farnesyl transferase inhibitors | Arglabin (NuOncology Labs)<br>Ionafarnib (Schering-Plough)<br>BAY-43-9006 (Bayer) | Tipifarnib (Johnson & Johnson)<br>Perillyl alcohol (DOR BioPharma) |
| Pump inhibitors | CBT-1 (CBA Pharma)<br>Tariquidar (Xenova)<br>MS-209 (Schering AG) | Zosuquidar trihydrochloride (Eli Lilly)<br>Biricodar dicitrate (Vertex) |
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT -3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/ antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (Ligand) | Alitretinoin (Ligand) |
| Immunomodulators | Interferon<br>Oncophage (Antigenics)<br>GMK (Progenies)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZD1839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca) | Kahalide F (PharmaMar)<br>CEP- 701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex) |

TABLE 1-continued

| | | |
|---|---|---|
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, AlIos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promoter, Pola) |
| | SRL-172 (T-cell stimulant, SR Pharma) | CHS-828 (cytotoxic agent, Leo) |
| | TLK-286 (glutathione-S transferase inhibitor, Telik) | Trans-retinic acid (differentiator, NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter, La Roche) |
| | SDX-101 (apoptosis promoter, Salmedix) | Brostallicin (apoptosis promoter, Pharmacia) |
| | Ceflatonin (apoptosis promoter, ChemGenex) | |

A combined treatment of this type can be achieved with the aid of simultaneous, consecutive or separate dispensing of the individual components of the treatment. Combination products of this type employ the compounds according to the invention.

V. GENERAL SYNTHESES

The compounds of the invention are prepared in general by methods known to those of skill in the art for synthesizing analogous compounds. These are illustrated by the general schemes indicated below, and the preparative examples that follow. Most starting materials are commercially available from supply companies like Aldrich Chemicals Co. or Sigma Chemical Company, as examples. Compounds that are not commercially available may be synthesized by those of skill in the art by following procedures given in references such as "*Organic Reactions*," Volumes 1-40, John Wiley & Sons (1991); "*Rodd's Chemistry of Carbon Compounds*," Volumes 1-5 and Suppl., Elservier Science Publishers (1989); "*Fieser and Fieser's Reagents for Organic Synthesis*," Volume 1-15, John Wiley & Sons (1991); "*Advanced Organic Chemistry*,"

Jerry March, John Wiley & Sons, 4th Ed. (1992); Lücking et al, *ChemMedChem* 2007, 2, 63-77; and Nicolaou. et al. *Agew. Chem. Int. Ed.* 2005, 44, 4490-4527. All compounds of the present invention were synthesized by processes developed by the inventors.
Scheme 1
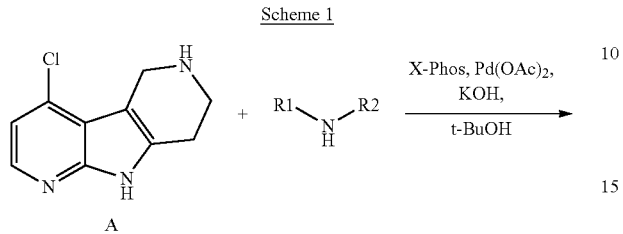
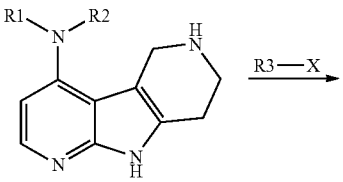
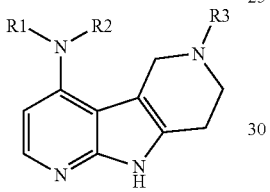
Scheme 2
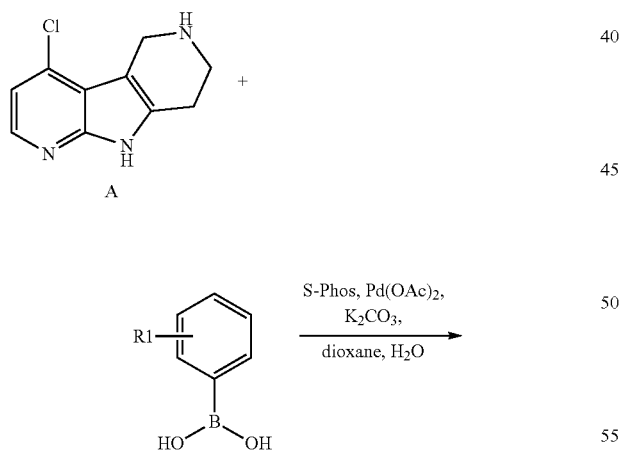
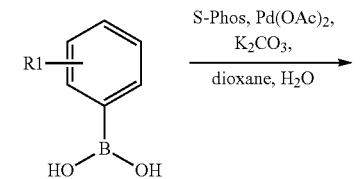
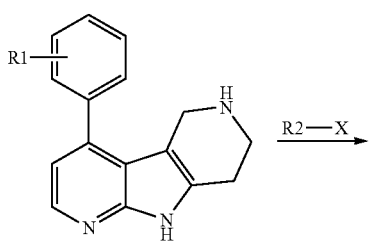
-continued
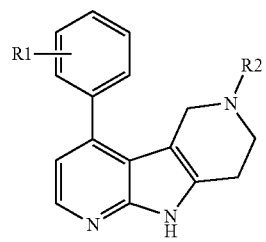
Scheme 3
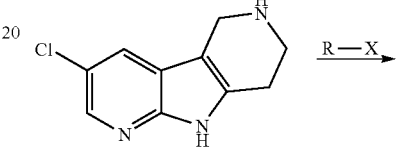
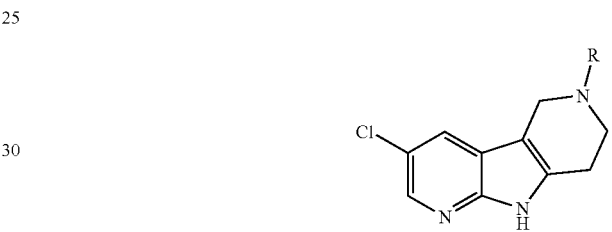
Scheme 4
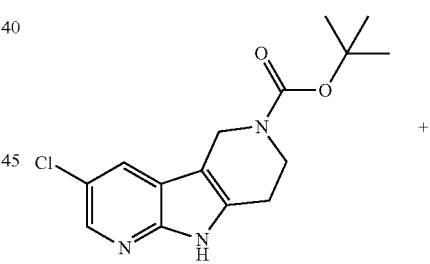
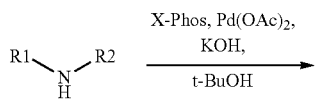
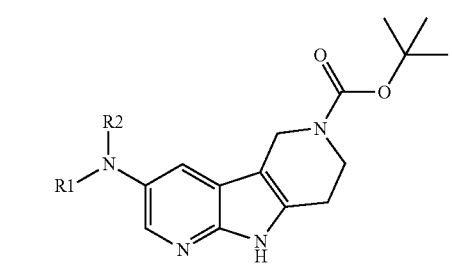

VI. EXAMPLES

Example 1

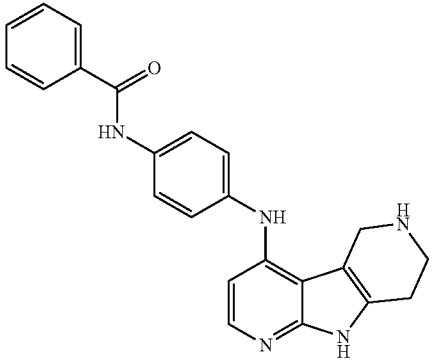 [SMILES: O=C(Nc1ccc(Nc2ccnc3[nH]c4c(c23)CNCC4)cc1)c1ccccc1]

N-[4-(6,7,8,9-Tetrahydro-5H-dipyrido[2,3-b;3',4'-d]
pyrrol-4-ylamino)-phenyl]-benzamide (1)

4-Chloro-6,7,8,9-tetrahydro-5H-dipyrido[2,3-b;3',4'-d]
pyrrole (500 mg, 1.78 mmol), N-(4-Amino-phenyl)-benzamide (454 mg, 2.14 mmol), $Pd(OAc)_2$ (20 mg, 0.09 mmol), X-Phos (85 mg, 0.18 mmol), and KOH (300 mg, 5.35 mmol) were dissolved in tert-butanol (9.0 mL), and stirred overnight at 100° C. The reaction mixture was concentrated, and then suspended in $EtOAc/H_2O$. The resulting precipitate was filtered, washed with $EtOAc/H_2O$, and dried under vacuum to provide 1 (255 mg, 37% yield) as a tan solid. LC-MS (M+H=384, obsd.=384).

Example 2

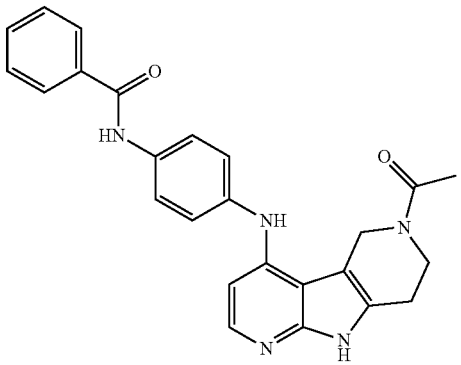 [SMILES: CC(=O)N1CCc2[nH]c3nccc(Nc4ccc(NC(=O)c5ccccc5)cc4)c3c2C1]

N-[4-(6-Acetyl-6,7,8,9-tetrahydro-5H-dipyrido[2,3-b;3',4'-d]pyrrol-4-y amino)-phenyl]-benzamide (2)

N-[4-(6,7,8,9-Tetrahydro-5H-dipyrido[2,3-b;3',4'-d]pyrrol-4-ylamino)-phenyl]-benzamide (40 mg, 0.1 mmol), acetic anhydride (13 mg, 0.13 mmol), and triethylamine (0.04 mL, 0.31 mmol) were dissolved in 1,2-dichloroethane (2.0 mL), and stirred overnight at room temperature. The reaction mixture was added directly to a Biotage column. The crude product was purified via Biotage eluting with $CH_2Cl_2$/MeOH (9/1, v/v) to provide 2 (7 mg, 16% yield) as an off-white solid. LC-MS (M+H=426, obsd.=426).

Example 3

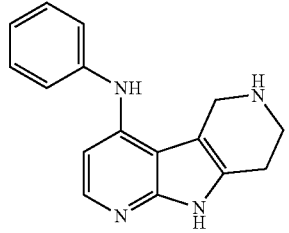 [SMILES: c1ccc(Nc2ccnc3[nH]c4c(c23)CNCC4)cc1]

Phenyl-(6,7,8,9-tetrahydro-5H-dipyrido[2,3-b;3',4'-d]pyrrol-4-yl)-amine (3)

4-Chloro-6,7,8,9-tetrahydro-5H-dipyrido[2,3-b;3',4'-d]
pyrrole (100 mg, 0.48 mmol), aniline (0.13 mL, 1.44 mmol), $Pd(OAc)_2$ (5 mg, 0.02 mmol), X-Phos (23 mg, 0.05 mmol), and KOH (162 mg, 2.89 mmol) were dissolved in tert-butanol (2.0 mL), and stirred overnight at 100° C. The reaction mixture diluted with $EtOAc/H_2O$, and filtered through an Extrelut column. The column was washed with EtOAc, and the filtrate was concentrated. The crude material was triturated with EtOAc, filtered, washed with EtOAc, and dried under vacuum to provide 3 (63 mg, 50% yield) as a tan solid. LC-MS (M+H=265, obsd.=265).

Example 4

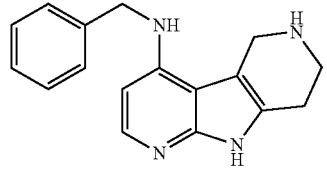 [SMILES: c1ccc(CNc2ccnc3[nH]c4c(c23)CNCC4)cc1]

Benzyl-(6,7,8,9-tetrahydro-5H-dipyrido[2,3-b;3',4'-d]pyrrol-4-yl)-amine (4)

4-Chloro-6,7,8,9-tetrahydro-5H-dipyrido[2,3-b;3',4'-d]
pyrrole (100 mg, 0.48 mmol), benzylamine (0.16 mL, 1.44 mmol), $Pd(OAc)_2$ (5 mg, 0.02 mmol), X-Phos (23 mg, 0.05 mmol), and KOH (162 mg, 2.89 mmol) were dissolved in tert-butanol (2.0 mL), and stirred overnight at 100° C. The reaction mixture diluted with $EtOAc/H_2O$, and filtered through an Extrelut column. The column was washed with EtOAc, and the filtrate was concentrated. The crude material was triturated with EtOAc, filtered, washed with EtOAc, and dried under vacuum to provide 4 (12 mg, 9% yield) as a tan solid. LC-MS (M+H=279, obsd.=279).

Example 5

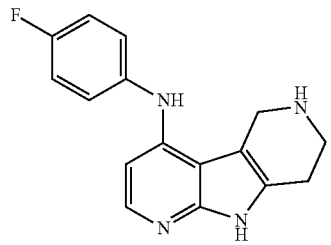 [SMILES: Fc1ccc(Nc2ccnc3[nH]c4c(c23)CNCC4)cc1]

(4-Fluoro-phenyl)-(6,7,8,9-tetrahydro-5H-dipyrido [2,3-b;3',4'-d]pyrrol-4-yl)-amine (5)

4-Chloro-6,7,8,9-tetrahydro-5H-dipyrido[2,3-b;3',4'-d] pyrrole (100 mg, 0.48 mmol), 4-fluoroaniline (0.14 mL, 1.44 mmol), Pd(OAc)$_2$ (5 mg, 0.02 mmol), 2-X-Phos (23 mg, 0.05 mmol), and KOH (162 mg, 2.89 mmol) were dissolved in tert-butanol (2.0 mL), and stirred overnight at 100° C. The reaction mixture diluted with EtOAc/H$_2$O, and filtered through an Extrelut column. The column was washed with EtOAc, and the filtrate was concentrated. The crude material was triturated with EtOAc, filtered, washed with EtOAc, and dried under vacuum to provide 5 (35 mg, 26% yield) as a brown solid. LC-MS (M+H=283, obsd.=283).

Example 6

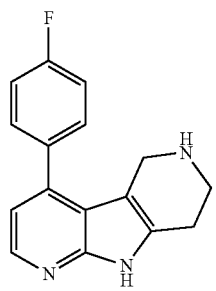 [SMILES: Fc1ccc(-c2ccnc3[nH]c4c(c23)CNCC4)cc1]

4-(4-Fluoro-phenyl)-6,7,8,9-tetrahydro-5H-dipyrido [2,3-b;3',4'-d]pyrrole (6)

4-Chloro-6,7,8,9-tetrahydro-5H-dipyrido[2,3-b;3',4'-d] pyrrole (100 mg, 0.48 mmol), 4-fluorophenylboronic acid (135 mg, 0.96 mmol), Pd(OAc)$_2$ (5 mg, 0.02 mmol), S-Phos (20 mg, 0.05 mmol), and K$_2$CO$_3$ (266 mg, 1.93 mmol) were dissolved in dioxane/H$_2$O (2.2 mL, 10/1, v/v), and stirred overnight at 100° C. The reaction mixture diluted with EtOAc/H$_2$O, and filtered through an Extrelut column. The column was washed with EtOAc, and the filtrate was concentrated. The crude material was triturated with EtOAc, filtered, washed with EtOAc, and dried under vacuum to provide 6 (37 mg, 29% yield) as a tan solid. LC-MS (M+H=269, obsd.=269).

Example 7

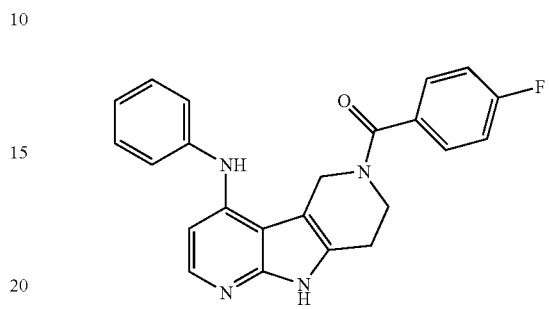

(4-Fluoro-phenyl)-(4-phenylamino-5,7,8,9-tetrahydro-dipyrido[2,3-b;3',4'-d]pyrrol-6-yl)-methanone (7)

Phenyl-(6,7,8,9-tetrahydro-5H-dipyrido[2,3-b;3',4'-d]pyrrol-4-yl)-amine (25 mg, 0.09 mmol), 4-fluorobenzoyl chloride (18 mg, 0.11 mmol), and triethylamine (0.04 mL, 0.28 mmol) were dissolved in 1,2-dichloroethane (2.0 mL), and stirred overnight at room temperature. The reaction mixture was added directly to a Biotage column. The crude product was purified via Biotage eluting with CH$_2$Cl$_2$/MeOH (9/1, v/v) to provide 7 (33 mg, 90% yield) as a tan solid. LC-MS (M+H=388, obsd.=388).

Example 8

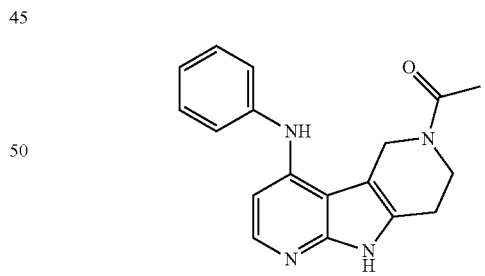

1-(4-Phenylamino-5,7,8,9-tetrahydro-dipyrido[2,3-b; 3',4'-d]pyrrol-6-yl)-ethanone (8)

Phenyl-(6,7,8,9-tetrahydro-5H-dipyrido[2,3-b;3',4'-d]pyrrol-4-yl)-amine (40 mg, 0.15 mmol), acetic anhydride (18 mg, 0.18 mmol), and triethylamine (0.06 mL, 0.45 mmol) were dissolved in 1,2-dichloroethane (2.0 mL), and stirred overnight at room temperature. The reaction mixture was added directly to a Biotage column. The crude product was

Example 9

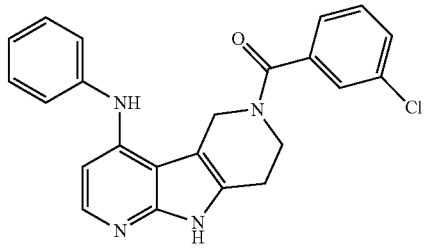 [SMILES: O=C(c1cccc(Cl)c1)N1CCc2[nH]c3nccc(Nc4ccccc4)c3c2C1]

(3-Chloro-phenyl)-(4-phenylamino-5,7,8,9-tetrahydro-dipyrido[2,3-b;3',4'-d]pyrrol-6-yl)-methanone (9)

Phenyl-(6,7,8,9-tetrahydro-5H-dipyrido[2,3-b;3',4'-d]pyrrol-4-yl)-amine (40 mg, 0.15 mmol), 3-chlorobenzoyl chloride (32 mg, 0.18 mmol), and triethylamine (0.06 mL, 0.45 mmol) were dissolved in 1,2-dichloroethane (2.0 mL), and stirred overnight at room temperature. The reaction mixture was added directly to a Biotage column. The crude product was purified via Biotage eluting with $CH_2Cl_2$/MeOH (9/1, v/v) to provide 9 (16 mg, 26% yield) as a tan solid. LC-MS (M+H=403, obsd.=403).

Example 10

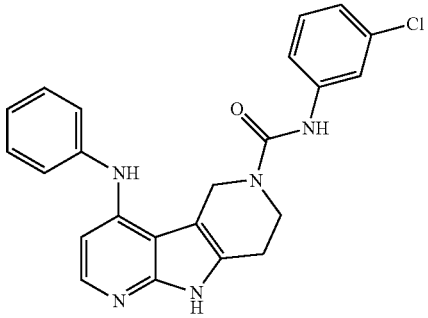 [SMILES: O=C(Nc1cccc(Cl)c1)N1CCc2[nH]c3nccc(Nc4ccccc4)c3c2C1]

4-Phenylamino-5,7,8,9-tetrahydro-dipyrido[2,3-b;3',4'-d]pyrrole-6-carboxylic acid (3-chloro-phenyl)-amide (10)

Phenyl-(6,7,8,9-tetrahydro-5H-dipyrido[2,3-b;3',4'-d]pyrrol-4-yl)-amine (40 mg, 0.15 mmol), 3-chlorophenyl isocyanate (28 mg, 0.18 mmol), and triethylamine (0.06 mL, 0.45 mmol) were dissolved in 1,2-dichloroethane (2.0 mL), and stirred overnight at room temperature. The reaction mixture was added directly to a Biotage column. The crude product was purified via Biotage eluting with $CH_2Cl_2$/MeOH (9/1, v/v) to provide 10 (16 mg, 25% yield) as an off-white solid. LC-MS (M+H=418, obsd.=418).

Example 11

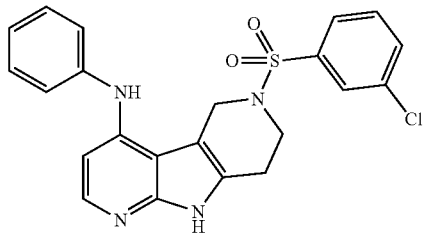 [SMILES: O=S(=O)(c1cccc(Cl)c1)N1CCc2[nH]c3nccc(Nc4ccccc4)c3c2C1]

[6-(3-Chloro-benzenesulfonyl)-6,7,8,9-tetrahydro-5H-dipyrido[2,3-b;3',4'-d]pyrrol-4-yl]-phenyl-amine (11)

Phenyl-(6,7,8,9-tetrahydro-5H-dipyrido[2,3-b;3',4'-d]pyrrol-4-yl)-amine (40 mg, 0.15 mmol), 3-chlorophenylsulfonyl chloride (38 mg, 0.18 mmol), and triethylamine (0.06 mL, 0.45 mmol) were dissolved in 1,2-dichloroethane (2.0 mL), and stirred overnight at room temperature. The reaction mixture was added directly to a Biotage column. The crude product was purified via Biotage eluting with $CH_2Cl_2$/MeOH (9/1, v/v) to provide 11 (15 mg, 23% yield) as a brown solid. LC-MS (M+H=439, obsd.=439).

Example 12

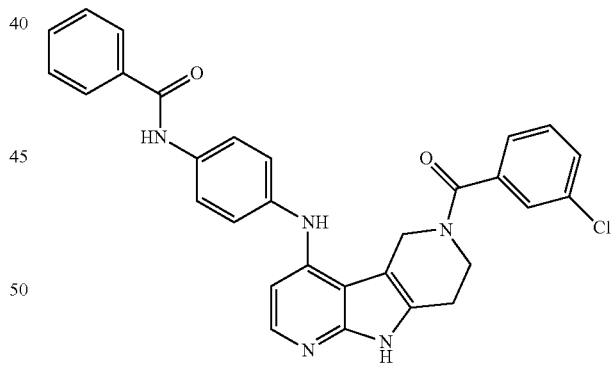

N-{4-[6-(3-Chloro-benzoyl)-6,7,8,9-tetrahydro-5H-dipyrido[2,3-b;3',4'-d]pyrrol-4-ylamino]-phenyl}-benzamide (12)

N-[4-(6,7,8,9-Tetrahydro-5H-dipyrido[2,3-b;3',4'-d]pyrrol-4-ylamino)-phenyl]-benzamide (40 mg, 0.1 mmol), 3-chlorobenzoyl chloride (22 mg, 0.13 mmol), and triethylamine (0.04 mL, 0.31 mmol) were dissolved in 1,2-dichloroethane (2.0 mL), and stirred overnight at room temperature. The reaction mixture was added directly to a Biotage column. The crude product was purified via Biotage eluting with CH$_2$Cl$_2$/MeOH (9/1, v/v) to provide 12 (26 mg, 48% yield) as a brown solid. LC-MS (M+H=522, obsd.=522).

Example 13

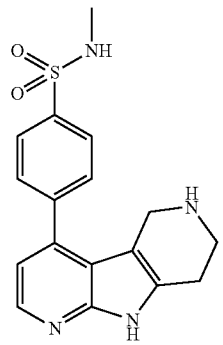 [SMILES: CNS(=O)(=O)c1ccc(-c2ccnc3[nH]c4c(c23)CNCC4)cc1]

N-Methyl-4-(6,7,8,9-tetrahydro-5H-dipyrido[2,3-b;3',4'-d]pyrrol-4-yl)-benzenesulfonamide (13)

4-Chloro-6,7,8,9-tetrahydro-5H-dipyrido[2,3-b;3',4'-d]pyrrole (150 mg, 0.61 mmol), (4-methylaminosulfonyl)phenyllboronic acid (264 mg, 1.23 mmol), Pd(OAc)$_2$ (7 mg, 0.03 mmol), S-Phos (25 mg, 0.06 mmol), and K$_2$CO$_3$ (340 mg, 2.46 mmol) were dissolved in dioxane/H$_2$O (2.2 mL, 10/1, v/v), and stirred overnight at 100° C. The reaction mixture diluted with EtOAc/H$_2$O. The resulting precipitate was filtered, washed with EtOAc, and dried under vacuum to provide 13 (107 mg, 51% yield) as a yellow solid. LC-MS (M+H=343, obsd.=343).

Example 14

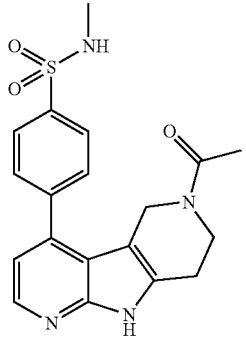 [SMILES: CNS(=O)(=O)c1ccc(-c2ccnc3[nH]c4c(c23)CN(C(C)=O)CC4)cc1]

4-(6-Acetyl-6,7,8,9-tetrahydro-5H-dipyrido[2,3-b;3',4'-d]pyrrol-4-yl)-N-methyl-benzenesulfonamide (14)

N-Methyl-4-(6,7,8,9-tetrahydro-5H-dipyrido[2,3-b;3',4'-d]pyrrol-4-yl)-benzenesulfonamide (75 mg, 0.22 mmol), acetic anhydride (22 mg, 0.22 mmol), and DIEA (0.07 mL, 0.44 mmol) were dissolved in dioxane (2.0 mL), and stirred for 2 h at room temperature. The reaction mixture was diluted with EtOAc/H2O. The resulting precipitate was filtered, washed with EtOAc, and dried under vacuum to provide 14 (40 mg, 48% yield) as a tan solid. LC-MS (M+H=385, obsd.=385).

Example 15

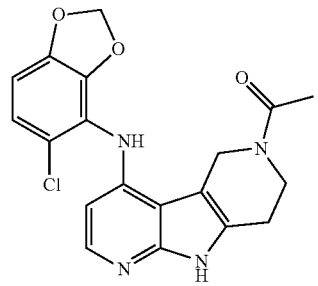 [SMILES: CC(=O)N1CCc2[nH]c3nccc(Nc4c(Cl)ccc5c4OCO5)c3c2C1]

1-[4-(5-Chloro-benzo[1,3]dioxol-4-ylamino)-5,7,8,9-tetrahydro-dipyrido[2,3-b;3',4'-d]pyrrol-6-yl]-ethanone (15)

4-Chloro-6,7,8,9-tetrahydro-5H-dipyrido[2,3-b;3',4'-d]pyrrole (150 mg, 0.61 mmol), 5-chloro-benzo[1,3]dioxol-4-ylamine (316 mg, 1.84 mmol), Pd(OAc)$_2$ (7 mg, 0.03 mmol), X-Phos (29 mg, 0.06 mmol), and KOH (276 mg, 4.92 mmol) were dissolved in tert-butanol (2.0 mL), and stirred overnight at 100° C. The reaction mixture diluted with EtOAc/H$_2$O, and filtered through an Extrelut column. The column was washed with EtOAc, and the filtrate was concentrated.

The crude product from above, acetic anhydride (45 mg, 0.44 mmol), and DIEA (0.15 mL, 0.88 mmol) were dissolved in dioxane (2.0 mL), and stirred overnight at room temperature. The reaction mixture was diluted with EtOAc/H$_2$O, and filtered through an Extrelut column. The column was washed with EtOAc, and the filtrate was concentrated. The crude product was purified via Biotage eluting with CH$_2$Cl$_2$/MeOH (9/1, v/v). The purified material was converted to HCl salt via dissolving in MeOH, addition of 1.5 M methanolic HCl, and concentration to provide 15 (20 mg, 10% overall yield) as a tan solid. LC-MS (M+H=385, obsd.=385).

Example 16

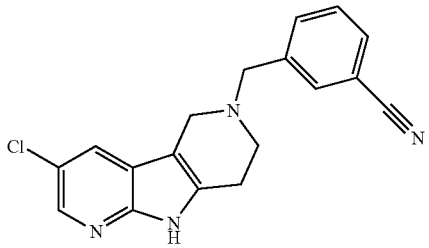 [SMILES: N#Cc1cccc(CN2CCc3[nH]c4ncc(Cl)cc4c3C2)c1]

3-(3-Chloro-5,7,8,9-tetrahydro-dipyrido[2,3-b;3',4'-d]pyrrol-6-ylmethyl)-benzonitrile (16)

3-Chloro-6,7,8,9-tetrahydro-5H-dipyrido[2,3-b;3',4'-d]pyrrole (50 mg; 0.24 mmol), 3-(bromomethyl)benzonitrile (56 mg; 0.29 mmol), and K$_2$CO$_3$ (0.04 ml; 0.72 mmol) where dissolved in DMF (2 ml) and stirred overnight at room temperature. Prep-LC-MS purification provided 16 as an off-white powder (21 mg, 27% yield). LC-MS (M+H=323, obsd.=323).

Example 17

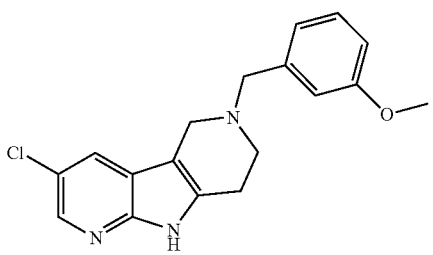 [SMILES: COc1cccc(CN2CCc3[nH]c4ncc(Cl)cc4c3C2)c1]

3-Chloro-6-(3-methoxy-benzyl)-6,7,8,9-tetrahydro-5H-dipyrido[2,3-b;3',4'-d]pyrrole (17)

3-Chloro-6,7,8,9-tetrahydro-5H-dipyrido[2,3-b;3',4'-d]pyrrole (50 mg; 0.24 mmol), 3-methoxybenzyl bromide (0.04 ml; 0.29 mmol), and K₂CO₃ (0.04 ml; 0.72 mmol) were dissolved in DMF (2 ml) and stirred overnight at room temperature. Prep-LC-MS purification provided 17 as an off-white powder (14 mg, 18% yield). LC-MS (M+H=328, obsd.=328).

Example 18

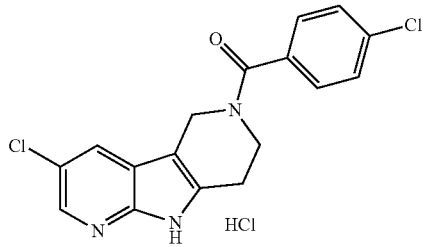 [SMILES: O=C(c1ccc(Cl)cc1)N1CCc2[nH]c3ncc(Cl)cc3c2C1 ; Cl]

(4-Chloro-phenyl)-(3-chloro-5,7,8,9-tetrahydro-dipyrido[2,3-b;3',4'-d]pyrrol-6-yl)-methanone.Hydrochloride Salt (18)

3-Chloro-6,7,8,9-tetrahydro-5H-dipyrido[2,3-b;3',4'-d]pyrrole (50 mg, 0.24 mmol) and DIEA (0.05 L, 0.29 mmol) were dissolved in THF (2 ml) and stirred at room temperature. 4-Chlorobenzoyl chloride (0.04 mL, 0.29 mmol) was added dropwise, and the reaction was stirred for 1 h at room temperature. The reaction was quenched with H₂O (200 mL). The crude resulting precipitate was filtered, and dried overnight under vacuum. The HCl salt was formed via dissolving the precipitate in MeOH (2 ml) and adding 1 M HCl/ether (2 equivalents), and cooling at 0° C. overnight. The resulting precipitate was filtered, and dried under vacuum to provide 18 (54 mg, 59% yield) as a yellow powder. LC-MS (M+H=346, obsd.=346).

Example 19

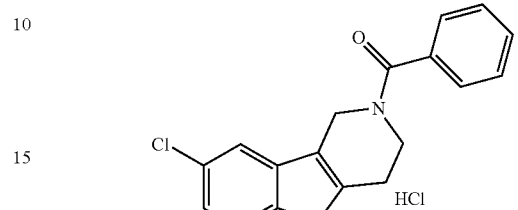

(3-Chloro-5,7,8,9-tetrahydro-dipyrido[2,3-b;3',4'-d]pyrrol-6-yl)-phenyl-methanone.Hydrochloride Salt (19)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2 ml). Benzoyl chloride (0.03 ml, 0.29 mmol) was added dropwise and the reaction was stirred at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 19 (33 mg, 40% yield) as a pale yellow solid. LC-MS (M+H=312, obsd.=312).

Example 20

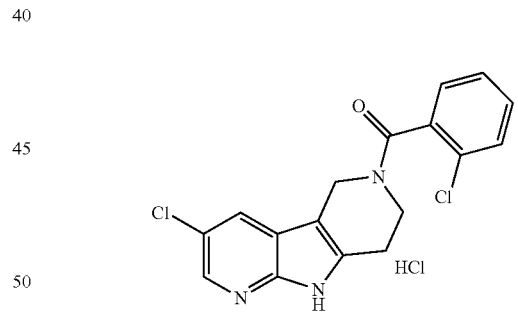

(2-Chloro-phenyl)-(3-chloro-5,7,8,9-tetrahydro-dipyrido[2,3-b;3',4'-d]pyrrol-6-yl)-methanone.Hydrochloride Salt (20)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2.00 ml). 2-Chlorobenzoyl chloride (0.04 mL, 0.29 mmol) was added dropwise, and the reaction mixture was stirred at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 20 (47 mg, 51% yield) as a pale yellow solid. LC-MS (M+H=347, obsd.=347).

Example 21

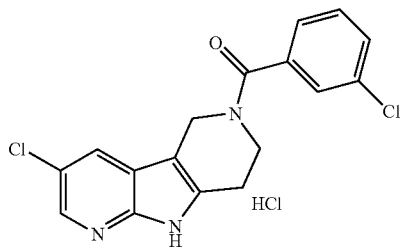 [SMILES: O=C(c1cccc(Cl)c1)N1CCc2[nH]c3ncc(Cl)cc3c2C1 ; Cl]

(3-Chloro-phenyl)-(3-chloro-5,7,8,9-tetrahydro-dipyrido[2,3-b;3',4'-d]pyrrol-6-yl)-methanone.Hydrochloride Salt (21)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2 mL). 3-Chlorobenzoyl chloride (0.04 mL, 0.29 mmol) was added dropwise, and the reaction solution was stirred at room temperature for 1 h. The crude reaction mixture was concentrated, and converted to the HCl salt by dissolving the crude material in MeOH (2 mL) and adding 1 M HCl/ether (2 equiv). The resulting solution was refrigerated overnight. The resulting precipitate was filtered and dried under vacuum to provide 21 (56 mg, 61% yield) as a pale yellow solid. LC-MS (M+H=347, obsd.=347).

Example 22

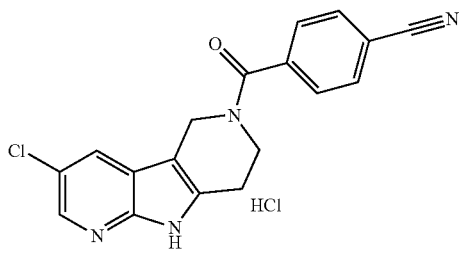 [SMILES: N#Cc1ccc(C(=O)N2CCc3[nH]c4ncc(Cl)cc4c3C2)cc1 ; Cl]

4-(3-Chloro-5,7,8,9-tetrahydro-dipyrido[2,3-b;3',4'-d]pyrrole-6-carbonyl)-benzonitrile.Hydrochloride Salt (22)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2 mL). 4-Cyanobenzoyl chloride (47.84 mg; 0.29 mmol) was added dropwise, and the reaction mixture was stirred at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 22 (40 mg, 45% yield) as a pale yellow solid. LC-MS (M+H=337, obsd.=337).

Example 23

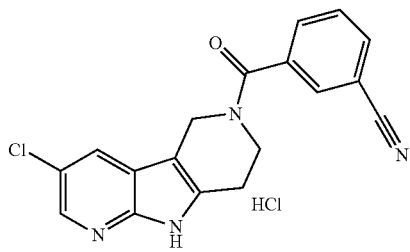 [SMILES: N#Cc1cccc(C(=O)N2CCc3[nH]c4ncc(Cl)cc4c3C2)c1 ; Cl]

3-(3-Chloro-5,7,8,9-tetrahydro-dipyrido[2,3-b;3',4'-d]pyrrole-6-carbonyl)-benzonitrile.Hydrochloride Salt (23)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2 mL). 3-Cyanobenzoyl chloride (48 mg, 0.29 mmol) was added dropwise, and the reaction solution was allowed to stir at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 23 (25 mg, 28% yield) as a pale yellow solid. LC-MS (M+H=337, obsd.=337).

Example 24

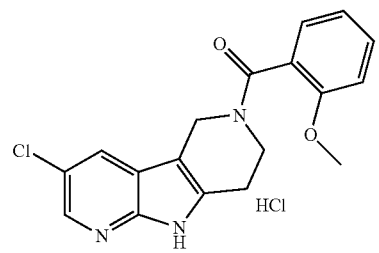 [SMILES: COc1ccccc1C(=O)N1CCc2[nH]c3ncc(Cl)cc3c2C1 ; Cl]

(3-Chloro-5,7,8,9-tetrahydro-dipyrido[2,3-b;3',4'-d]pyrrol-6-yl)-(2-methoxy-phenyl)-methanone.Hydrochloride Salt (24)

3-Chloro-6,7,8,9-tetrahydro-5H-dipyrido[2,3-b;3',4'-d]pyrrole (50 mg, 0.24 mmol) and DIEA (0.05 mL, 0.29 mmol) were dissolved in THF (2 mL). o-Anisoyl chloride (0.04 mL, 0.29 mmol) was added dropwise, and the reaction solution was stirred at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 24 (48 mg, 53% yield) as an off white solid. LC-MS (M+H=342, obsd.=342).

Example 25

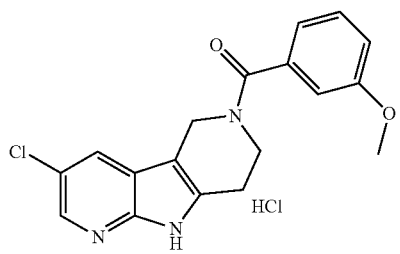 [SMILES: COc1cccc(C(=O)N2CCc3[nH]c4ncc(Cl)cc4c3C2)c1 ; Cl]

(3-Chloro-5,7,8,9-tetrahydro-dipyrido[2,3-b;3',4'-d] pyrrol-6-yl)-(3-methoxy-phenyl)-methanone.Hydrochloride Salt (25)

3-Chloro-6,7,8,9-tetrahydro-5H-dipyrido[2,3-b;3',4'-d] pyrrole (50 mg, 0.24 mmol) and DIEA (0.05 mL, 0.29 mmol) were dissolved in THF (2 mL). m-Anisoyl chloride (0.04 mL, 0.29 mmol) was added dropwise, and the reaction solution was stirred at room temperature for 1 h. The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 25 (50 mg, 55% yield) as an off white solid. LC-MS (M+H=342, obsd.=342).

Example 26

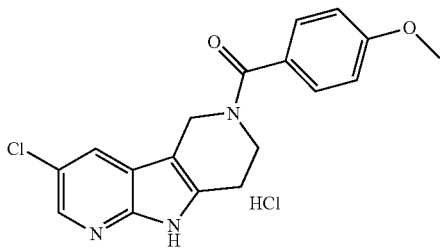 [SMILES: COc1ccc(C(=O)N2CCc3[nH]c4ncc(Cl)cc4c3C2)cc1 ; Cl]

(3-Chloro-5,7,8,9-tetrahydro-dipyrido[2,3-b;3',4'-d] pyrrol-6-yl)-(4-methoxy-phenyl)-methanone.Hydrochloride Salt (26)

3-Chloro-6,7,8,9-tetrahydro-5H-dipyrido[2,3-b;3',4'-d] pyrrole (50 mg, 0.24 mmol) and DIEA (0.05 mL, 0.29 mmol) were dissolved in THF (2 mL). p-Anisoyl chloride (0.04 mL, 0.29 mmol) was added dropwise, and the reaction solution was stirred at room temperature for 1 h The crude reaction mixture was concentrated, and converted to the HCl salt by dissolving the crude material in MeOH (2 ml) and adding 1 M HCl/ether (2 equiv). The resulting solution was refrigerated overnight. The resulting precipitate was filtered and dried under vacuum to provide 26 (49 mg, 54% yield) as an off white solid. LC-MS (M+H=342, obsd.=342).

Example 27

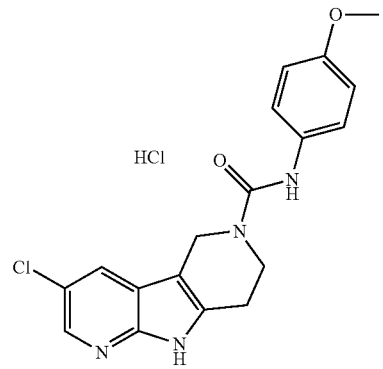 [SMILES: COc1ccc(NC(=O)N2CCc3[nH]c4ncc(Cl)cc4c3C2)cc1 ; Cl]

3-Chloro-5,7,8,9-tetrahydro-dipyrido[2,3-b;3',4'-d] pyrrole-6-carboxylic acid (4-methoxy-phenyl)-amide.Hydrochloride Salt (27)

3-Chloro-6,7,8,9-tetrahydro-5H-dipyrido[2,3-b;3',4'-d] pyrrole (50 mg, 0.24 mmol), and DIEA (0.04 mL, 0.24 mmol) were dissolved in DCM (2 mL). 4-Methoxyphenyl isocyanate (0.03 mL, 0.26 mmol) was added dropwise, and the reaction solution was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 27 (15 mg, 16% yield) as a yellow solid. LC-MS (M+H=359, obsd.=359).

Example 28

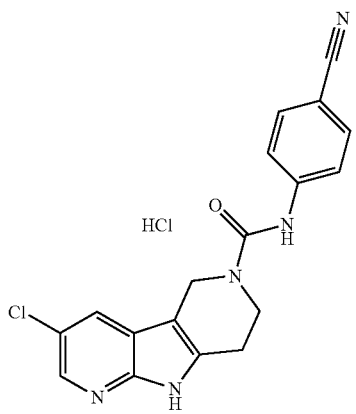 [SMILES: N#Cc1ccc(NC(=O)N2CCc3[nH]c4ncc(Cl)cc4c3C2)cc1 ; Cl]

3-Chloro-5,7,8,9-tetrahydro-dipyrido[2,3-b;3',4'-d] pyrrole-6-carboxylic acid (4-cyano-phenyl)-amide-.Hydrochloride Salt (28)

3-Chloro-6,7,8,9-tetrahydro-5H-dipyrido[2,3-b;3',4'-d] pyrrole (50 mg, 0.24 mmol), and DIEA (0.04 mL, 0.24 mmol)

were dissolved in DCM (2 mL). 4-Cyanophenyl isocyanate (34 mg, 0.24 mmol) was added and the reaction mixture was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 28 (60 mg, 64% yield) as a yellow solid. LC-MS (M+H=353, obsd.=353).

Example 29

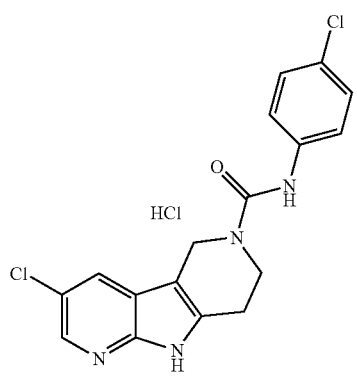 [SMILES: O=C(Nc1ccc(Cl)cc1)N1CCc2[nH]c3ncc(Cl)cc3c2C1 ; Cl]

3-Chloro-5,7,8,9-tetrahydro-dipyrido[2,3-b;3',4'-d]pyrrole-6-carboxylic acid (4-chloro-phenyl)-amide.Hydrochloride Salt (29)

3-Chloro-6,7,8,9-tetrahydro-5H-dipyrido[2,3-b;3',4'-d]pyrrole (50 mg, 0.24 mmol), and DIEA (0.04 mL, 0.24 mmol) were dissolved in DCM (2 mL). 4-Chlorophenyl isocyanate (0.03 mL, 0.26 mmol) was added dropwise, and the reaction solution was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 29 (54 mg, 57% yield) as a yellow solid. LC-MS (M+H=362, obsd.=362).

Example 30

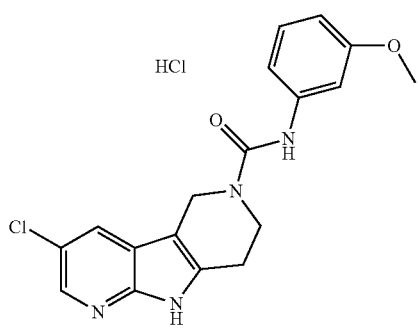 [SMILES: COc1cccc(NC(=O)N2CCc3[nH]c4ncc(Cl)cc4c3C2)c1 ; Cl]

3-Chloro-5,7,8,9-tetrahydro-dipyrido[2,3-b;3',4'-d]pyrrole-6-carboxylic acid (3-methoxy-phenyl)-amide.Hydrochloride Salt (30)

3-Chloro-6,7,8,9-tetrahydro-5H-dipyrido[2,3-b;3',4'-d]pyrrole (50 mg, 0.24 mmol), and DIEA (0.04 mL, 0.24 mmol) were dissolved in DCM (2 mL). 3-Methoxyphenyl isocyanate (0.03 mL, 0.24 mmol) was added dropwise, and the reaction solution was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 30 (28 mg, 30% yield) as a yellow solid. LC-MS (M+H=357, obsd.=357).

Example 31

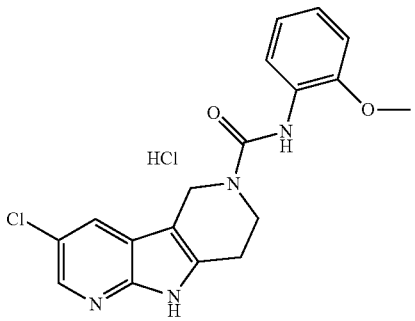 [SMILES: COc1ccccc1NC(=O)N1CCc2[nH]c3ncc(Cl)cc3c2C1 ; Cl]

3-Chloro-5,7,8,9-tetrahydro-dipyrido[2,3-b;3',4'-d]pyrrole-6-carboxylic acid (2-methoxy-phenyl)-amide.Hydrochloride Salt (31)

3-Chloro-6,7,8,9-tetrahydro-5H-dipyrido[2,3-b;3',4'-d]pyrrole (50 mg, 0.24 mmol), and DIEA (0.04 mL, 0.24 mmol) were dissolved in DCM (2 mL). 2-Methoxyphenyl isocyanate (0.03 mL, 0.24 mmol) was added dropwise, and the reaction solution was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 31 (32 mg, 33% yield) as a yellow solid. LC-MS (M+H=357, obsd.=357).

Example 32

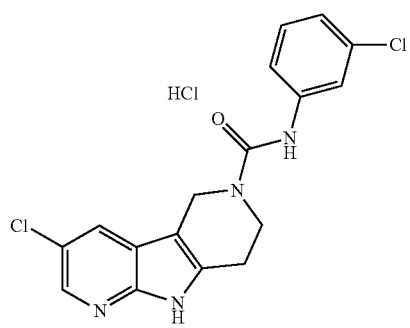 [SMILES: O=C(Nc1cccc(Cl)c1)N1CCc2[nH]c3ncc(Cl)cc3c2C1 ; Cl]

3-Chloro-5,7,8,9-tetrahydro-dipyrido[2,3-b;3',4'-d]pyrrole-6-carboxylic acid (3-chloro-phenyl)-amide-.Hydrochloride Salt (32)

3-Chloro-6,7,8,9-tetrahydro-5H-dipyrido[2,3-b;3',4'-d]pyrrole (50 mg, 0.24 mmol), and DIEA (0.04 mL, 0.24 mmol) were dissolved in DCM (2 mL). 3-Chlorophenyl isocyanate (0.03 mL, 0.26 mmol) was added dropwise, and the reaction solution was stirred overnight at room temperature. The crude reaction mixture was concentrated, and converted to the HCl salt by dissolving the crude material in MeOH (1 ml) and adding 1 M HCl/ether (2 equiv). The resulting solution was refrigerated overnight. Additional ether was added to drive precipitate formation. The resulting precipitate was filtered and dried under vacuum to provide 32 (54 mg, 56% yield) as a yellow solid. LC-MS (M+H=361, obsd.=361).

Example 33

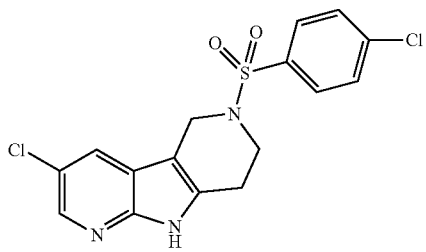 [SMILES: O=S(=O)(c1ccc(Cl)cc1)N1CCc2[nH]c3ncc(Cl)cc3c2C1]

3-Chloro-6-(4-chloro-benzenesulfonyl)-6,7,8,9-tetrahydro-5H-dipyrido[2,3-b;3',4'-d]pyrrole (33)

4-Chlorobenzenesulfonyl chloride (56 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 33 (92 mg, 99% yield) as a yellow solid. LC-MS (M+H=382, obsd.=382).

Example 34

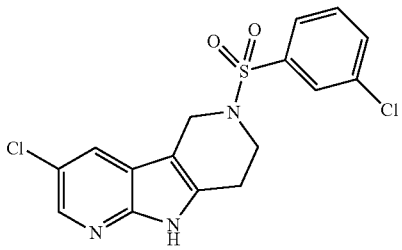 [SMILES: O=S(=O)(c1cccc(Cl)c1)N1CCc2[nH]c3ncc(Cl)cc3c2C1]

3-Chloro-6-(2-chloro-benzenesulfonyl)-6,7,8,9-tetrahydro-5H-dipyrido[2,3-b;3',4'-d]pyrrole (34)

3-Chlorobenzenesulfonyl chloride (56 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 34 (34 mg, 37% yield) as a yellow solid. LC-MS (M+H=382, obsd.=382).

Example 35

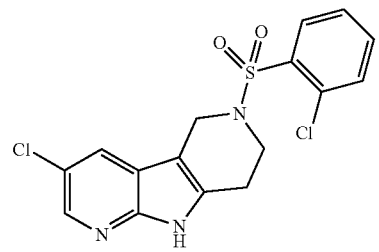 [SMILES: O=S(=O)(c1ccccc1Cl)N1CCc2[nH]c3ncc(Cl)cc3c2C1]

2-Chloro-6-(3-chloro-benzenesulfonyl)-6,7,8,9-tetrahydro-5H-dipyrido[2,3-b;3',4'-d]pyrrole (35)

2-Chlorobenzenesulfonyl chloride (56 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 35 (86 mg, 96% yield) as a yellow solid. LC-MS (M+H=382, obsd.=382).

Example 36

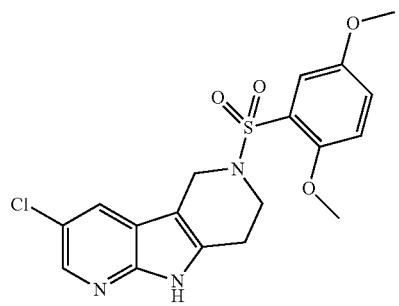 [SMILES: COc1ccc(OC)c(S(=O)(=O)N2CCc3[nH]c4ncc(Cl)cc4c3C2)c1]

3-Chloro-6-(2,5-dimethoxy-benzenesulfonyl)-6,7,8,9-tetrahydro-5H-dipyrido[2,3-b;3',4'-d]pyrrole (36)

2,5-Dimethoxybenzenesulfonyl chloride (63 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 36 (94 mg, 96% yield) as a yellow solid. LC-MS (M+H=408, obsd.=408).

Example 37

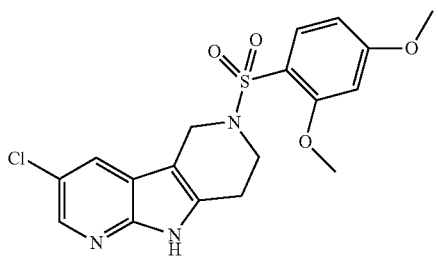 [SMILES: COc1ccc(S(=O)(=O)N2CCc3[nH]c4ncc(Cl)cc4c3C2)c(OC)c1]

3-Chloro-6-(2,4-dimethoxy-benzenesulfonyl)-6,7,8,9-tetrahydro-5H-dipyrido[2,3-b;3',4'-d]pyrrole (37)

2,5-Dimethoxybenzenesulfonyl chloride (63 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 37 (69 mg, 70% yield) as a yellow solid. LC-MS (M+H=408, obsd.=408).

Example 38

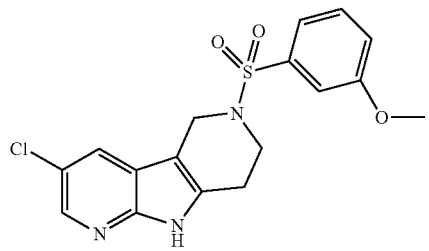 [SMILES: COc1cccc(S(=O)(=O)N2CCc3[nH]c4ncc(Cl)cc4c3C2)c1]

3-Chloro-6-(3-methoxy-benzenesulfonyl)-6,7,8,9-tetrahydro-5H-dipyrido[2,3-b;3',4'-d]pyrrole (38)

3-Methoxybenzenesulfonyl chloride (0.04 mL, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 38 (50 mg, 55% yield) as a yellow solid. LC-MS (M+H=379, obsd.=379).

Example 39

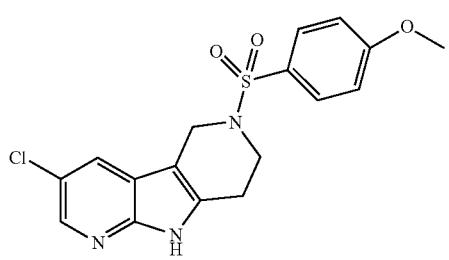 [SMILES: COc1ccc(S(=O)(=O)N2CCc3[nH]c4ncc(Cl)cc4c3C2)cc1]

3-Chloro-6-(4-methoxy-benzenesulfonyl)-6,7,8,9-tetrahydro-5H-dipyrido[2,3-b;3',4'-d]pyrrole (39)

4-Methoxybenzenesulfonyl chloride (0.04 mL, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 39 (61 mg, 67% yield) as a yellow solid. LC-MS (M+H=379, obsd.=379).

Example 40

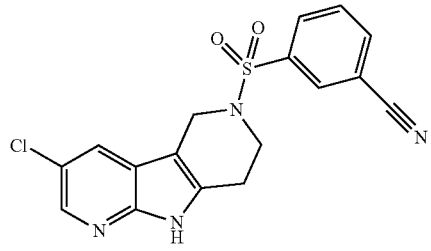 [SMILES: N#Cc1cccc(S(=O)(=O)N2CCc3[nH]c4ncc(Cl)cc4c3C2)c1]

3-(3-Chloro-5,7,8,9-tetrahydro-dipyrido[2,3-b;3',4'-d]pyrrole-6-sulfonyl)-benzonitrile (40)

3-Cyanobenzenesulfonyl chloride (53 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 40 (68 mg, 76% yield) as a yellow solid. LC-MS (M+H=373, obsd.=373).

Example 41

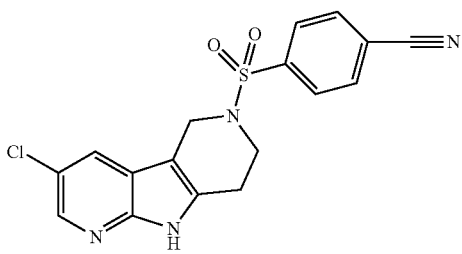 [SMILES: N#Cc1ccc(S(=O)(=O)N2CCc3[nH]c4ncc(Cl)cc4c3C2)cc1]

4-(3-Chloro-5,7,8,9-tetrahydro-dipyrido[2,3-b;3',4'-d]pyrrole-6-sulfonyl)-benzonitrile (41)

4-Cyanobenzenesulfonyl chloride (53 mg, 0.26 mmol) was added to a solution of 3-chloro-6,7,8,9-tetrahydro-5H-dipyrido[2,3-b;3',4'-d]pyrrole (50 mg, 0.24 mmol) in pyridine (2 mL), and the reaction was stirred overnight at room temperature. The reaction mixture was added to water (20 mL), and the resulting precipitate was filtered and dried under vacuum to provide 41 (55 mg, 62% yield) as a yellow solid. LC-MS (M+H=373, obsd.=373).

Example 42

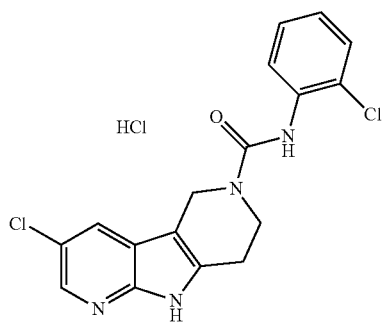 [SMILES: O=C(Nc1ccccc1Cl)N1CCc2[nH]c3ncc(Cl)cc3c2C1 ; Cl]

3-Chloro-5,7,8,9-tetrahydro-dipyrido[2,3-b;3',4'-d]pyrrole-6-carboxylic acid (2-chloro-phenyl)-amide-.Hydrochloride Salt (42)

3-Chloro-6,7,8,9-tetrahydro-5H-dipyrido[2,3-b;3',4'-d]pyrrole (50 mg, 0.24 mmol), and DIEA (0.04 mL, 0.24 mmol) were dissolved in DCM (2 mL). 2-Chlorophenyl isocyanate (0.03 mL, 0.26 mmol) was added dropwise, and the reaction solution was stirred overnight at room temperature. The crude reaction mixture was concentrated, and converted to the HCl salt by dissolving the crude material in MeOH (2 ml) and adding 1 M HCl/ether (2 equiv). The resulting solution was refrigerated overnight. Additional ether was added to drive precipitate formation. The resulting precipitate was filtered and dried under vacuum to provide 42 (52 mg, 55% yield). LC-MS (M+H=361, obsd.=361).

Example 43

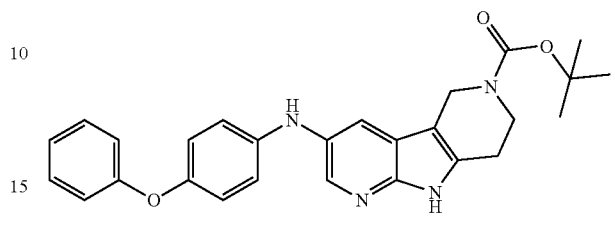

3-(4-Phenoxy-phenylamino)-5,7,8,9-tetrahydro-dipyrido[2,3-b;3',4'-d]pyrrole-6-carboxylic acid tert-butyl ester (43)

3-Chloro-5,7,8,9-tetrahydro-dipyrido[2,3-b;3',4'-d]pyrrole-6-carboxylic acid tert-butyl ester (100 mg, 0.32 mmol), 4-phenoxyaniline (120 mg, 0.65 mmol), Pd(OAc)$_2$ (3 mg, 0.01 mmol), X-Phos (12 mg, 0.03 mmol), and KOH (0.03 ml, 0.97 mmol) were suspended in tert-amyl alcohol (2 mL), and stirred overnight at 95° C. The crude mixture was added directly to a Biotage column. The crude product was purified via Biotage eluting with a gradient of 0 to 100% EtOAc in hexanes to provide 43 (39 mg, 26% yield) as a brown solid. LC-MS (M+H=457, obsd.=457).

Example 44

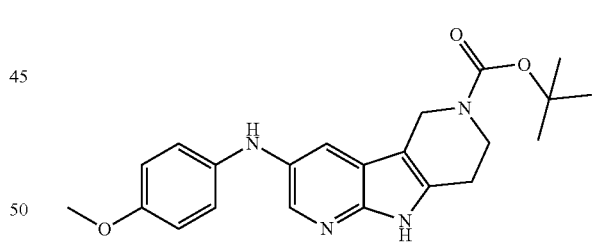

3-(4-Methoxy-phenylamino)-5,7,8,9-tetrahydro-dipyrido[2,3-b;3',4'-d]pyrrole-6-carboxylic acid tert-butyl ester (44)

3-Chloro-5,7,8,9-tetrahydro-dipyrido[2,3-b;3',4'-d]pyrrole-6-carboxylic acid tert-butyl ester (100 mg, 0.32 mmol), p-anisidine (48 mg, 0.39 mmol), Pd(OAc)$_2$ (3 mg, 0.01 mmol), X-Phos (12 mg, 0.03 mmol), and KOH (0.03 ml, 0.97 mmol) were suspended in tert-amyl alcohol (2 mL), and stirred overnight at 95° C. The crude mixture was added directly to a Biotage column. The crude product was purified via Biotage eluting with a gradient of 0 to 100% EtOAc in hexanes to provide 44 (16 mg, 13% yield) as a brown oil. LC-MS (M+H=395, obsd.=395).

Example 45

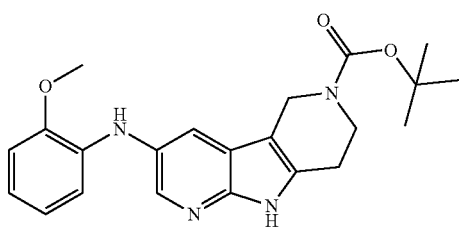 [SMILES: COc1ccccc1Nc1cnc2[nH]c3c(c2c1)CN(C(=O)OC(C)(C)C)CC3]

3-(2-Methoxy-phenylamino)-5,7,8,9-tetrahydro-dipyrido[2,3-b;3',4'-d]pyrrole-6-carboxylic acid tert-butyl ester (45)

3-Chloro-5,7,8,9-tetrahydro-dipyrido[2,3-b;3',4'-d]pyrrole-6-carboxylic acid tert-butyl ester (100 mg, 0.32 mmol), o-anisidine (48 mg, 0.39 mmol), Pd(OAc)$_2$ (3 mg, 0.01 mmol), X-Phos (12 mg, 0.03 mmol), and KOH (0.03 ml, 0.97 mmol) were suspended in tert-amyl alcohol (2 mL), and stirred overnight at 95° C. The crude mixture was added directly to a Biotage column. The crude product was purified via Biotage eluting with a gradient of 0 to 100% EtOAc in hexanes to provide 45 (9 mg, 7% yield) as a brown oil. LC-MS (M+H=395, obsd.=395).

Example 46

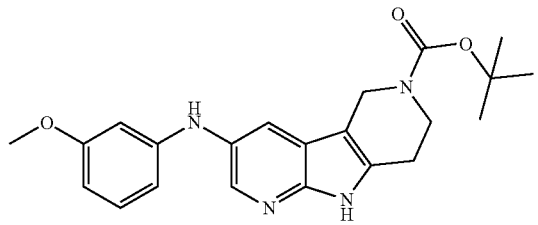 [SMILES: COc1cccc(Nc2cnc3[nH]c4c(c3c2)CN(C(=O)OC(C)(C)C)CC4)c1]

3-(3-Methoxy-phenylamino)-5,7,8,9-tetrahydro-dipyrido[2,3-b;3',4'-d]pyrrole-6-carboxylic acid tert-butyl ester (46)

3-Chloro-5,7,8,9-tetrahydro-dipyrido[2,3-b;3',4'-d]pyrrole-6-carboxylic acid tert-butyl ester (100 mg, 0.32 mmol), m-anisidine (0.04 mL, 0.39 mmol), Pd(OAc)$_2$ (3 mg, 0.01 mmol), X-Phos (12 mg, 0.03 mmol), and KOH (0.03 ml, 0.97 mmol) were suspended in tert-amyl alcohol (2 mL), and stirred overnight at 95° C. The crude mixture was added directly to a Biotage column. The crude product was purified via Biotage eluting with a gradient of 0 to 100% EtOAc in hexanes to provide 46 (6 mg, 5% yield) as a brown oil. LC-MS (M+H=395, obsd.=395).

Example 47

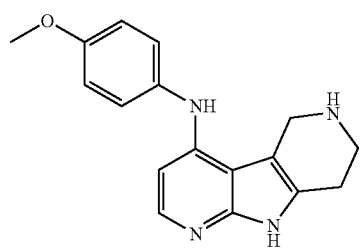 [SMILES: COc1ccc(Nc2ccnc3[nH]c4c(c23)CNCC4)cc1]

(4-Methoxy-phenyl)-(6,7,8,9-tetrahydro-5H-dipyrido[2,3-b;3',4'-d]pyrrol-4-yl)-amine (47)

4-Chloro-5,7,8,9-tetrahydro-dipyrido[2,3-b;3',4'-d]pyrrole-6-carboxylic acid tert-butyl ester (100 mg, 0.32 mmol), p-anisidine (80 mg, 0.65 mmol), Pd(OAc)$_2$ (3 mg, 0.01 mmol), X-Phos (12 mg, 0.03 mmol), and KOH (55 mg, 0.97 mmol) were suspended in tert-amyl alcohol (2 mL), and stirred overnight at 95° C. The crude product was purified directly via prep-LC-MS to provide 47 (3 mg, 3% yield) as a tan solid. LC-MS (M+H=295, obsd.=295).

Example 48

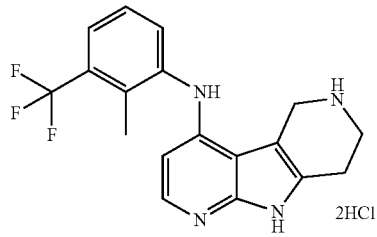 [SMILES: Cc1c(Nc2ccnc3[nH]c4c(c23)CNCC4)cccc1C(F)(F)F]

(2-Methyl-3-trifluoromethyl-phenyl)-(6,7,8,9-tetrahydro-5H-dipyrido[2,3-b;3',4'-d]pyrrol-4-yl)-amine.bis-hydrochloride Salt (48)

4-Chloro-6,7,8,9-tetrahydro-5H-dipyrido[2,3-b; 3',4'-d]pyrrole.bishydrochloride (200 mg, 0.71 mmol), 2-methyl-3-(trifluoromethyl)aniline (150 mg, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 48 (109 mg, 36% yield) as a yellow solid. LC-MS (M+H=347, obsd.=347).

Example 49

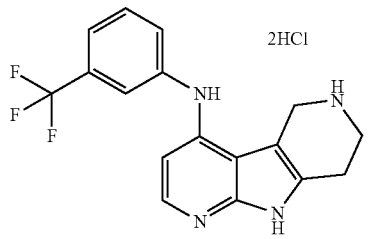 [SMILES: FC(F)(F)c1cccc(Nc2ccnc3[nH]c4c(c23)CNCC4)c1]

(6,7,8,9-Tetrahydro-5H-dipyrido[2,3-b;3',4'-d]pyrrol-4-yl)-(3-trifluoromethyl-phenyl)-amine.Bishydrochloride Salt (49)

4-Chloro-6,7,8,9-tetrahydro-5H-dipyrido[2,3-b;3',4'-d]pyrrole.bishydrochloride (200 mg, 0.71 mmol), 3-(trifluoromethyl)aniline (0.11 mL, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 49 (18 mg, 6% yield) as a grey solid. LC-MS (M+H=333, obsd.=333).

Example 50

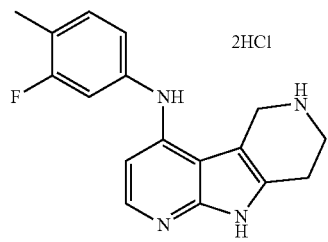 [SMILES: Cc1ccc(Nc2ccnc3[nH]c4c(c23)CNCC4)cc1F]

(3-Fluoro-4-methyl-phenyl)-(6,7,8,9-tetrahydro-5H-dipyrido[2,3-b;3',4'-d]pyrrol-4-yl)-amine.Bishydrochloride Salt (50)

4-Chloro-6,7,8,9-tetrahydro-5H-dipyrido[2,3-b;3',4'-d]pyrrole.bishydrochloride (200 mg, 0.71 mmol), 3-fluoro-4-methylaniline (0.10 mL, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 50 (6 mg, 2% yield) as a grey solid. LC-MS (M+H=297, obsd.=297).

Example 51

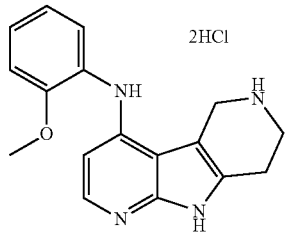 [SMILES: COc1ccccc1Nc1ccnc2[nH]c3c(c12)CNCC3]

(2-Methoxy-phenyl)-(6,7,8,9-tetrahydro-5H-dipyrido[2,3-b;3',4'-d]pyrrol-4-yl)-amine.Bishydrochloride Salt (51)

4-Chloro-6,7,8,9-tetrahydro-5H-dipyrido[2,3-b;3',4'-d]pyrrole.bishydrochloride (200 mg, 0.71 mmol), o-anisidine (0.10 mL, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 51 (20 mg, 8% yield) as a grey solid. LC-MS (M+H=295, obsd.=295).

Example 52

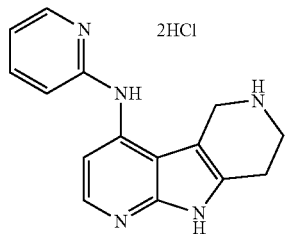 [SMILES: c1ccc(Nc2ccnc3[nH]c4c(c23)CNCC4)nc1]

Pyridin-2-yl-(6,7,8,9-tetrahydro-5H-dipyrido[2,3-b;3',4'-d]pyrrol-4-yl)-amine.Bishydrochloride Salt (52)

4-Chloro-6,7,8,9-tetrahydro-5H-dipyrido[2,3-b;3',4'-d]pyrrole.bishydrochloride (200 mg, 0.71 mmol), 2-aminopyridine (81 mg, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 52 (32 mg, 13% yield) as a light brown solid. LC-MS (M+H=266, obsd.=266).

Example 53

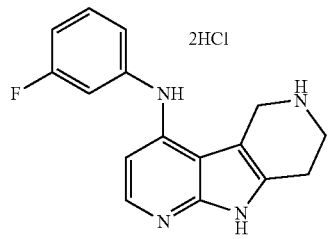 [SMILES: Fc1cccc(Nc2ccnc3[nH]c4c(c23)CNCC4)c1]

(3-Fluoro-phenyl)-(6,7,8,9-tetrahydro-5H-dipyrido [2,3-b;3',4'-d]pyrrol-4-yl)-amine.Bishydrochloride Salt (53)

4-Chloro-6,7,8,9-tetrahydro-5H-dipyrido[2,3-b;3',4'-d] pyrrole.bishydrochloride (200 mg, 0.71 mmol), 3-fluoroaniline (0.08 mL, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 53 (41 mg, 16% yield) as a brown solid. LC-MS (M+H=282, obsd.=282).

Example 54

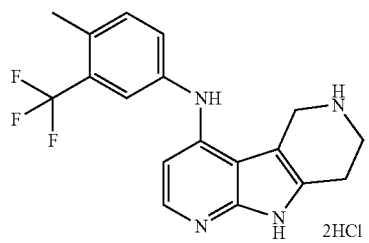 [SMILES: Cc1ccc(Nc2ccnc3[nH]c4c(c23)CNCC4)cc1C(F)(F)F]

(4-Methyl-3-trifluoromethyl-phenyl)-(6,7,8,9-tetrahydro-5H-dipyrido[2,3-b;3',4'-d]pyrrol-4-yl)-amine.Bishydrochloride Salt (54)

4-Chloro-6,7,8,9-tetrahydro-5H-dipyrido[2,3-b;3',4'-d] pyrrole.bishydrochloride (200 mg, 0.71 mmol), 3-(trifluoromethyl)-4-methylaniline (0.12 mL, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 54 (31 mg, 10% yield) as a grey solid. LC-MS (M+H=347, obsd.=347).

Example 55

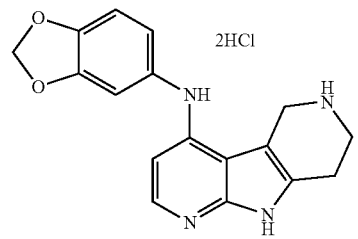 [SMILES: c1cc(Nc2ccc3c(c2)OCO3)c2c3c([nH]c2n1)CCNC3]

Benzo[1,3]dioxol-5-yl-(6,7,8,9-tetrahydro-5H-dipyrido[2,3-b;3',4'-d]pyrrol-4-yl)-amine.Bishydrochloride Salt (55)

4-Chloro-6,7,8,9-tetrahydro-5H-dipyrido[2,3-b;3',4'-d] pyrrole.bishydrochloride (200 mg, 0.71 mmol), 3,4-(methylenedioxy)aniline (117 mg, 0.86 mmol), Pd(OAc)$_2$ (8 mg, 0.04 mmol), X-Phos (34 mg, 0.07 mmol), and KOH (240 mg, 4.28 mmol) were suspended in tert-butanol (3 mL), and stirred overnight at 100° C. The reaction was concentrated, and the reaction mixture was suspended in DMSO (1 mL) and H$_2$O (15 mL). The resulting precipitate was filtered, and dissolved in MeOH (2 mL) and 2M HCl in ether (3 equiv). Ether (10 mL) was added dropwise to the solution to induce precipitate formation. The resulting precipitate was filtered to provide 54 (33 mg, 12% yield) as a brown solid. LC-MS (M+H=309, obsd.=309).

Example 56

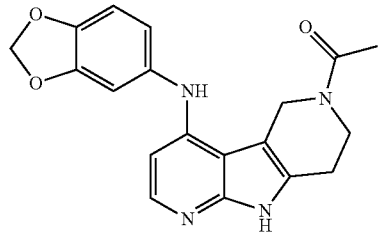 [SMILES: CC(=O)N1CCc2[nH]c3nccc(Nc4ccc5c(c4)OCO5)c3c2C1]

1-[4-(Benzo[1,3]dioxol-5-ylamino)-5,7,8,9-tetrahydro-dipyrido[2,3-b;3',4'-d]pyrrol-6-yl]-ethanone (56)

Benzo[1,3]dioxol-5-yl-(6,7,8,9-tetrahydro-5H-dipyrido [2,3-b;3',4'-d]pyrrol-4-yl)-amine (50 mg, 0.16 mmol), acetic anhydride (18 µL, 0.19 mmol), and triethylamine (67 µL, 0.49 mmol) were dissolved in 1,2-dichloroethane (2 mL), and stirred overnight at room temperature. The reaction mixture was added directly to a Biotage column. The crude product was purified via Biotage eluting with a gradient of 0 to 10%

MeOH in DCM. Lyophilization of the purified product provided 56 (25 mg, 44% yield) as a tan powder. LC-MS (M+H=351, obsd.=351).

product provided 58 (9 mg, 14% yield) as a tan powder. LC-MS (M+H=339, obsd.=339).

Example 57

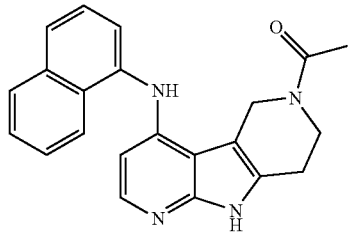 [SMILES: CC(=O)N1CCc2[nH]c3nccc(Nc4cccc5ccccc45)c3c2C1]

1-[4-(Naphthalen-1-ylamino)-5,7,8,9-tetrahydro-dipyrido[2,3-b;3',4'-d]pyrrol-6-yl]-ethanone (57)

Naphthalen-1-yl-(6,7,8,9-tetrahydro-5H-dipyrido[2,3-b;3',4'-d]pyrrol-4-yl)-amine (40 mg, 0.13 mmol), acetic anhydride (12 μL, 0.13 mmol), and triethylamine (53 μL, 0.38 mmol) were dissolved in 1,2-dichloroethane (2 mL), and stirred for 3 h at room temperature. The reaction mixture was added directly to a Biotage column. The crude product was purified via Biotage eluting with a gradient of 0 to 10% MeOH in DCM. Lyophilization of the purified product provided 57 (10 mg, 22% yield) as a tan powder. LC-MS (M+H=357, obsd.=357).

Example 58

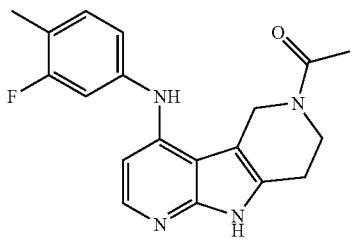 [SMILES: CC(=O)N1CCc2[nH]c3nccc(Nc4ccc(C)c(F)c4)c3c2C1]

1-[4-(3-Fluoro-4-methyl-phenylamino)-5,7,8,9-tetrahydro-dipyrido[2,3-b;3',4'-d]pyrrol-6-yl]-ethanone (58)

(3-Fluoro-4-methyl-phenyl)-(6,7,8,9-tetrahydro-5H-dipyrido[2,3-b;3',4'-d]pyrrol-4-yl)-amine (50 mg, 0.17 mmol), acetic anhydride (17 μL, 0.17 mmol), and triethylamine (70 μL, 0.51 mmol) were dissolved in 1,2-dichloroethane (2 mL), and stirred overnight at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified

Example 59

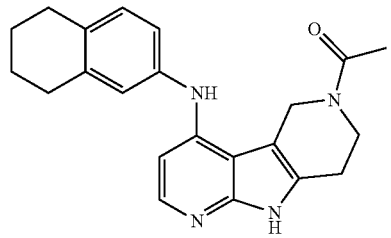 [SMILES: CC(=O)N1CCc2[nH]c3nccc(Nc4ccc5c(c4)CCCC5)c3c2C1]

1-[4-(5,6,7,8-Tetrahydro-naphthalen-2-ylamino)-5,7,8,9-tetrahydro-dipyrido[2,3-b;3',4'-d]pyrrol-6-yl]-ethanone (59)

(6,7,8,9-Tetrahydro-5H-dipyrido[2,3-b;3',4'-d]pyrrol-4-yl)-(5,6,7,8-tetrahydro-naphthalen-2-yl)-amine (75 mg, 0.24 mmol), acetic anhydride (25 μL, 0.24 mmol), and triethylamine (98 μL, 0.71 mmol) were dissolved in 1,2-dichloroethane (2 mL), and stirred for 30 min at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified product provided 59 (22 mg, 26% yield) as a tan powder. LC-MS (M+H=361, obsd.=361).

Example 60

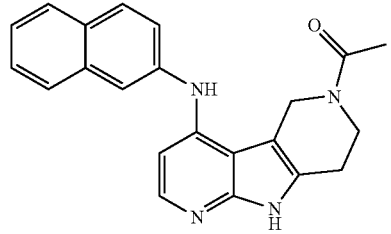 [SMILES: CC(=O)N1CCc2[nH]c3nccc(Nc4ccc5ccccc5c4)c3c2C1]

1-[4-(Naphthalen-2-ylamino)-5,7,8,9-tetrahydro-dipyrido[2,3-b;3',4'-d]pyrrol-6-yl]-ethanone (60)

Naphthalen-2-yl-(6,7,8,9-tetrahydro-5H-dipyrido[2,3-b;3',4'-d]pyrrol-4-yl)-amine (79 mg, 0.25 mmol), acetic anhydride (25 μL, 0.25 mmol), and triethylamine (104 μL, 0.75 mmol) were dissolved in 1,2-dichloroethane (2 mL), and stirred for 30 min at room temperature. The reaction was quenched with $H_2O$, and the resulting material was filtered through an Extrelut column. The column was washed with EtOAc, and the filtrate was concentrated. The crude material was purified via Biotage eluting with a gradient of 0 to 10%

MeOH in DCM. Lyophilization of the purified product provided 60 (24 mg, 26% yield) as a tan powder. LC-MS (M+H=357, obsd.=357).

Example 61

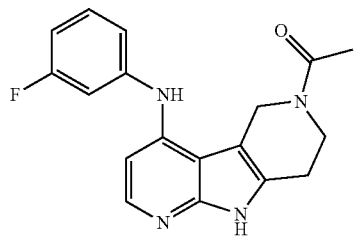 [SMILES: CC(=O)N1CCc2[nH]c3nccc(Nc4cccc(F)c4)c3c2C1]

1-[4-(3-Fluoro-phenylamino)-5,7,8,9-tetrahydro-dipyrido[2,3-b;3',4'-d]pyrrol-6-yl]-ethanone (61)

(3-Fluoro-phenyl)-(6,7,8,9-tetrahydro-5H-dipyrido[2,3-b;3',4'-d]pyrrol-4-yl)-amine (15 mg, 0.05 mmol), acetic anhydride (53 µL, 0.05 mmol), and triethylamine (22 µL, 0.16 mmol) were dissolved in 1,2-dichloroethane (2 mL), and stirred for 30 min at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified product provided 61 (3 mg, 15% yield) as an oily residue. LC-MS (M+H=325, obsd.=325).

Example 62

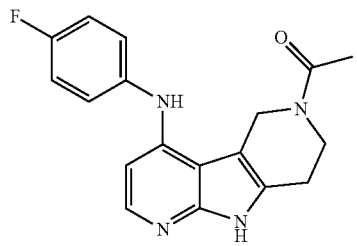 [SMILES: CC(=O)N1CCc2[nH]c3nccc(Nc4ccc(F)cc4)c3c2C1]

1-[4-(4-Fluoro-phenylamino)-5,7,8,9-tetrahydro-dipyrido[2,3-b;3',4'-d]pyrrol-6-yl]-ethanone (62)

(4-Fluoro-phenyl)-(6,7,8,9-tetrahydro-5H-dipyrido[2,3-b;3',4'-d]pyrrol-4-yl)-amine (45 mg, 0.16 mmol), acetic anhydride (16 µL, 0.16 mmol), and triethylamine (66 µL, 0.48 mmol) were dissolved in 1,2-dichloroethane (2 mL), and stirred for 30 min at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified product provided 62 (7 mg, 13% yield) as a oily residue. LC-MS (M+H=325, obsd.=325).

Example 63

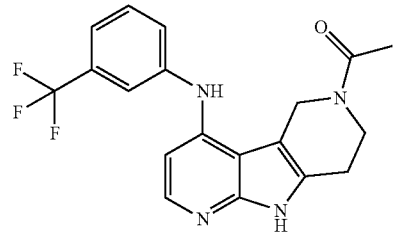 [SMILES: CC(=O)N1CCc2[nH]c3nccc(Nc4cccc(C(F)(F)F)c4)c3c2C1]

1-[4-(3-Trifluoromethyl-phenylamino)-5,7,8,9-tetrahydro-dipyrido[2,3-b;3',4'd]pyrrol-6-yl]-ethanone (63)

(6,7,8,9-Tetrahydro-5H-dipyrido[2,3-b;3',4'-d]pyrrol-4-yl)-(3-trifluoromethyl-phenyl)-amine (40 mg, 0.12 mmol), acetic anhydride (12 µL, 0.12 mmol), and triethylamine (50 µL, 0.36 mmol) were dissolved in 1,2-dichloroethane (2 mL), and stirred for 30 min at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified product provided 63 (7 mg, 16% yield) as an oily residue. LC-MS (M+H=375, obsd.=375).

Example 64

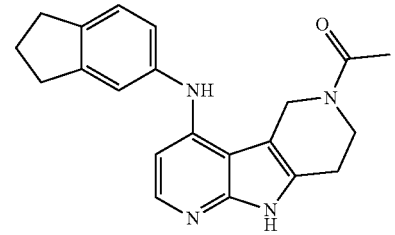 [SMILES: CC(=O)N1CCc2[nH]c3nccc(Nc4ccc5c(c4)CCC5)c3c2C1]

1-[4-(Indan-5-ylamino)-5,7,8,9-tetrahydro-dipyrido[2,3-b;3',4'-d]pyrrol-6-yl]-ethanone (64)

Indan-5-yl-(6,7,8,9-tetrahydro-5H-dipyrido[2,3-b;3',4'-d]pyrrol-4-yl)-amine (75 mg, 0.25 mmol), acetic anhydride (25 µL, 0.25 mmol), and triethylamine (102 µL, 0.74 mmol) were dissolved in 1,2-dichloroethane (2 mL), and stirred for 30 min at room temperature. The reaction was quenched with $H_2O$, and the resulting material was filtered through an Extrelut column. The Extrelut column was washed with EtOAc, and the filtrate was concentrated. The crude material was purified via Biotage eluting with a gradient of 0 to 10% MeOH in DCM. Lyophilization of the purified product provided 64 (21 mg, 25% yield) as an oily residue. LC-MS (M+H=347, obsd.=347).

Example 65

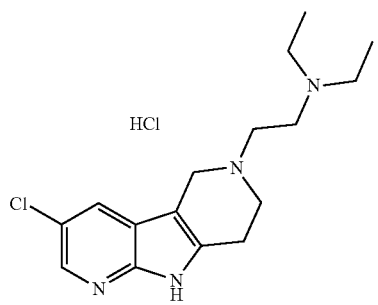 [SMILES: CCN(CC)CCN1CCc2[nH]c3ncc(Cl)cc3c2C1 ; Cl]

[2-(3-Chloro-5,7,8,9-tetrahydro-dipyrido[2,3-b;3',4'-d]pyrrol-6-yl)-ethyl]-diethyl-amine.Hydrochloride Salt (65)

3-Chloro-6,7,8,9-tetrahydro-5H-dipyrido[2,3-b;3',4'-d]pyrrole (100 mg, 0.48 mmol), 2-diethylaminoethyl chloride hydrochloride (91 mg, 0.53 mmol), $K_2CO_3$ (0.08 mL, 1.44 mmol), and NaI (0.02 mL, 0.53 mmol) were suspended in DMF (2 mL), and stirred overnight at room temperature. The reaction solution was diluted with $H_2O$, and extracted with EtOAc. The organic extracts were washed with brine, dried over $MgSO_4$, filtered, and concentrated. The crude product was converted into the HCl salt by dissolving in MeOH and adding 2M HCl in ether (2 equiv.) dropwise. The resulting precipitate was filtered to provide 65 (54 mg, 37% yield) as a white solid. LC-MS (M+H=307, obsd.=307).

Example 66

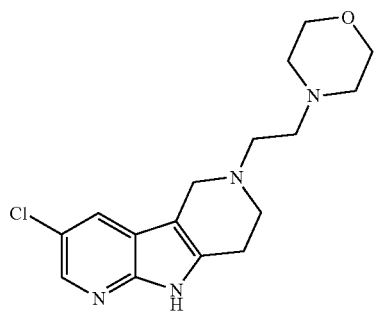 [SMILES: Clc1cnc2[nH]c3c(c2c1)CN(CCN1CCOCC1)CC3]

3-Chloro-6-(2-morpholin-4-yl-ethyl)-6,7,8,9-tetrahydro-5H-dipyrido[2,3-b;3',4'-d]pyrrole (66)

3-Chloro-6,7,8,9-tetrahydro-5H-dipyrido[2,3-b;3',4'-d]pyrrole (100 mg, 0.48 mmol), 4-(2-chloroethyl)morpholine hydrochloride (99 mg, 0.53 mmol), $K_2CO_3$ (0.08 mL, 1.44 mmol), and NaI (0.02 mL; 0.53 mmol) were suspended in DMF (2 mL). The reaction solution was diluted with $H_2O$, and extracted with EtOAc. The organic extracts were washed with brine, dried over $MgSO_4$, filtered, and concentrated to provide 66 (66 mg, 43% yield) as a yellow solid. LC-MS (M+H=321, obsd.=321).

Example 67

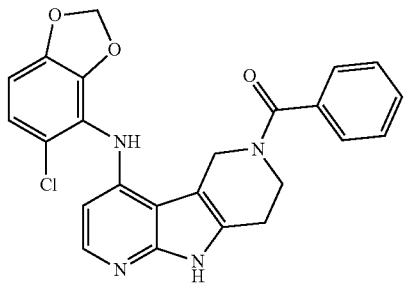 [SMILES: O=C(c1ccccc1)N1CCc2[nH]c3nccc(Nc4c(Cl)ccc5c4OCO5)c3c2C1]

[4-(5-Chloro-benzo[1,3]-dioxol-4-ylamino)-5,7,8,9-tetrahydro-dipyrido[2,3-b;3',4'-d]pyrrol-6-yl]-phenyl-methanone (67)

(5-Chloro-benzo[1,3]dioxol-4-yl)-(6,7,8,9-tetrahydro-5H-dipyrido[2,3-b;3',4'-d]pyrrol-4-yl)-amine (100 mg, 0.29 mmol) and DIEA (0.15 mL, 0.88 mmol) were dissolved in 1,2-dichloroethane (2 mL) and stirred at room temperature. Benzoyl chloride (0.03 mL, 0.35 mmol) was added dropwise, and the reaction was stirred for 1 h at room temperature. The reaction solution was concentrated. The crude material was dissolved in DMSO (3 mL) and filtered. The filtrate was purified directly via prep-LC-MS to provide 67 (13 mg, 10% yield) as a white fluffy solid. LC-MS (M+H=447, obsd.=447).

Example 68

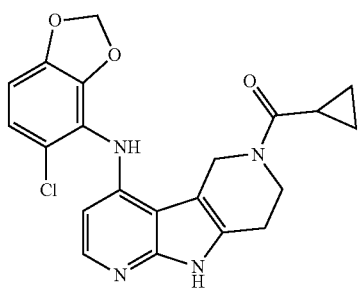 [SMILES: O=C(C1CC1)N1CCc2[nH]c3nccc(Nc4c(Cl)ccc5c4OCO5)c3c2C1]

[4-(5-Chloro-benzo[1,3]-dioxol-4-ylamino)-5,7,8,9-tetrahydro-dipyrido[2,3-b;3',4'-d]pyrrol-6-yl]-cyclopropyl-methanone (68)

(5-Chloro-benzo[1,3]-dioxol-4-yl)-(6,7,8,9-tetrahydro-5H-dipyrido[2,3-b;3',4'-d]pyrrol-4-yl)-amine (100 mg, 0.29 mmol) and DIEA (0.15 mL, 0.88 mmol) were dissolved in 1,2-dichloroethane (2 mL) and stirred at room temperature. Cyclopropanecarbonyl chloride (0.03 mL, 0.35 mmol) was added dropwise, and the reaction was stirred for 1 h at room temperature. The reaction was concentrated. The crude material was dissolved in DMSO (3 mL) and filtered. The filtrate was purified directly via prep-LC-MS to provide 68 (42 mg, 35% yield) as a white fluffy solid. LC-MS (M+H=411, obsd.=411).

Example 69

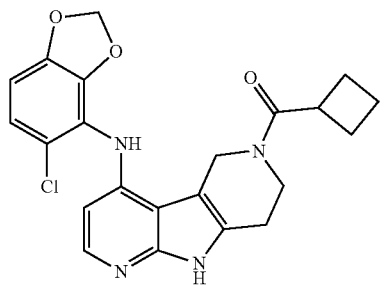 [SMILES: O=C(C1CCC1)N1CCc2[nH]c3nccc(Nc4c(Cl)ccc5c4OCO5)c3c2C1]

[4-(5-Chloro-benzo[1,3]-dioxol-4-ylamino)-5,7,8,9-tetrahydro-dipyrido[2,3-b;3',4'-d]pyrrol-6-yl]-cyclobutyl-methanone (69)

(5-Chloro-benzo[1,3]dioxol-4-yl)-(6,7,8,9-tetrahydro-5H-dipyrido[2,3-b;3',4'-d]pyrrol-4-yl)-amine (100 mg, 0.29 mmol) and DIEA (0.15 mL, 0.88 mmol) were dissolved in 1,2-dichloroethane (2 mL) and stirred at room temperature. Cyclobutanecarbonyl chloride (0.04 mL, 0.35 mmol) was added dropwise, and the reaction was stirred for 1 h at room temperature. The reaction was concentrated. The crude material was dissolved in DMSO (3 mL) and filtered. The filtrate was purified directly via prep-LC-MS to provide 69 (37 mg, 30% yield) as a white fluffy solid. LC-MS (M+H=425, obsd.=425).

Example 70

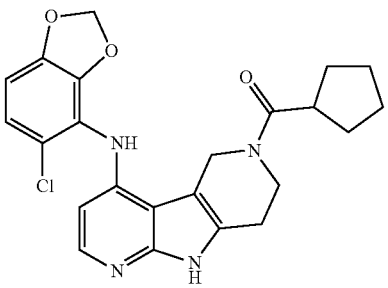 [SMILES: O=C(C1CCCC1)N1CCc2[nH]c3nccc(Nc4c(Cl)ccc5c4OCO5)c3c2C1]

[4-(5-Chloro-benzo[1,3]-dioxol-4-ylamino)-5,7,8,9-tetrahydro-dipyrido[2,3-b;3',4'-d]pyrrol-6-yl]-cyclopentyl-methanone (70)

(5-Chloro-benzo[1,3]dioxol-4-yl)-(6,7,8,9-tetrahydro-5H-dipyrido[2,3-b;3',4'-d]pyrrol-4-yl)-amine (100 mg, 0.29 mmol) and DIEA (0.15 mL, 0.88 mmol) were dissolved in 1,2-dichloroethane (2 mL) and stirred at room temperature. Cyclopentanecarbonyl chloride (0.04 mL, 0.35 mmol) was added dropwise, and the reaction was stirred for 1 h at room temperature. The reaction was concentrated. The crude material was dissolved in DMSO (3 mL) and filtered. The filtrate was purified directly via prep-LC-MS to provide 70 (43 mg, 33% yield) as a white fluffy solid. LC-MS (M+H=439, obsd.=439).

Example 71

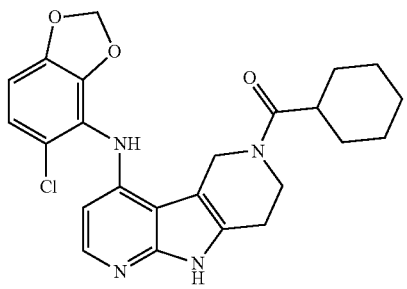 [SMILES: O=C(C1CCCCC1)N1CCc2[nH]c3nccc(Nc4c(Cl)ccc5c4OCO5)c3c2C1]

[4-(5-Chloro-benzo[1,3]-dioxol-4-ylamino)-5,7,8,9-tetrahydro-dipyrido[2,3-b;3',4'-d]pyrrol-6-yl]-cyclohexyl-methanone (71)

(5-Chloro-benzo[1,3]-dioxol-4-yl)-(6,7,8,9-tetrahydro-5H-dipyrido[2,3-b;3',4'-d]pyrrol-4-yl)-amine (75 mg, 0.22 mmol) and DIEA (0.11 mL, 0.66 mmol) were dissolved in 1,2-dichloroethane (2 mL) and stirred at room temperature. Cyclohexanecarbonyl chloride (0.04 mL, 0.26 mmol) was added dropwise, and the reaction was stirred for 1 h at room temperature. The reaction was concentrated. The crude material was dissolved in DMSO (3 mL) and filtered. The filtrate was purified directly via prep-LC-MS to provide 71 (43 mg, 33% yield) as a white fluffy solid. LC-MS (M+H=453, obsd.=453).

Example 72

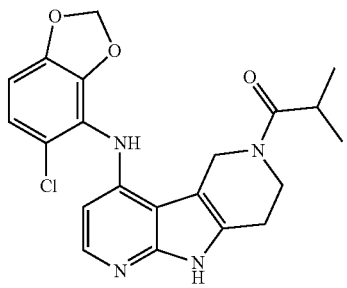 [SMILES: CC(C)C(=O)N1CCc2[nH]c3nccc(Nc4c(Cl)ccc5c4OCO5)c3c2C1]

1-[4-(5-Chloro-benzo[1,3]dioxol-4-ylamino)-5,7,8,9-tetrahydro-dipyrido[2,3-b;3',4'-d]pyrrol-6-yl]-2-methyl-propan-1-one (72)

(5-Chloro-benzo[1,3]dioxol-4-yl)-(6,7,8,9-tetrahydro-5H-dipyrido[2,3-b;3',4'-d]pyrrol-4-yl)-amine (75 mg, 0.22 mmol) and DIEA (0.11 mL, 0.66 mmol) were dissolved in 1,2-dichloroethane (2 mL) and stirred at room temperature. Isobutyryl chloride (0.03 mL, 0.26 mmol) was added dropwise, and the reaction was stirred for 1 h at room temperature. The reaction was concentrated. The crude material was dissolved in DMSO (3 mL) and filtered. The filtrate was purified directly via prep-LC-MS to provide 72 (14 mg, 15% yield) as a white fluffy solid. LC-MS (M+H=413, obsd.=413).

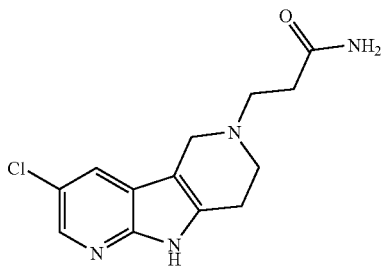 [SMILES: NC(=O)CCN1CCc2[nH]c3ncc(Cl)cc3c2C1]

Example 73

Synthesis of: 3-(3-Chloro-5,7,8,9-tetrahydro-dipyrido[2,3-b;3',4'-d]pyrrol-6-yl)-propionamide Intermediate 73.1: 3-Chloro-6,7,8,9-tetrahydro-5H-dipyrido[2,3-b;3',4'-d]pyrrole To a solution of 3-chloro-5,7,8,9-tetrahydro-dipyrido[2,3-b;3',4'-d]pyrrole-6-carboxylic acid tert-butyl ester (1.00 g; 3.25 mmol) in methanol (50 mL) was added a solution of hydrogen chloride (16.3 ml; 2 M; 32.5 mmol) in diethyl ether. The yellow solution was stirred at 25° C. for 3 days and a beige precipitate slowly formed. Ether (50 mL) was added and the beige suspension was stirred for 15 min. The precipitate was filtered, washed with ether and dried under vacuo to afford the hydrochloride salt of intermediate 1.1 (992 mg, 98%) as a beige solid (HPLC: 99.9%, RT: 1.18 min) $^1$H NMR (DMSO-d6) δ 11.99 (br s, 1H), 9.68 (br s, 2H), 8.17 (d, J=2.6 Hz, 1H), 8.08 (d, J=2.2 Hz, 1H), 4.26 (br s, 2H), 3.45 (br q, J=5.9 Hz, 2H), 3.05 (br t, J=5.9 Hz, 2H); MS (m/z) 208 [M+H]$^+$ ($^{35}$Cl).

Example 73

3-(3-Chloro-5,7,8,9-tetrahydro-dipyrido[2,3-b;3',4'-d]pyrrol-6-yl)-propionamide

To a suspension of intermediate 1.1 (100 mg; 0.36 mmol) and 3-chloropropionamide (42.2 mg; 0.39 mmol) in anhydrous DMF (2 mL) was added potassium carbonate (148 mg; 1.07 mmol) and sodium iodide (59 mg; 0.39 mmol). The resulting reaction mixture was stirred at 50° C. temperature for 3 days and concentrated under vacuo. The residue was purified by chromatography on a Biotage KP-NH column with a Isolera system, using dichloromethane and methanol as eluents to afford the title compound (59 mg, 59%) as a white solid (HPLC: 91%, RT: 0.54 min) $^1$H NMR (DMSO-d6, rotamers) δ 11.58 (br s, 1H, major rotamer), 11.52 (br s, 1H, minor rotamer), 8.06 (dd, J=4.8, 2.2 Hz, 1H), 7.85 (d, J=2.2 Hz), 7.40 (br s, 1H), 6.80 (br s, 1H), 3.81 (br s, 2H, minor rotamer), 3.56 (br s, 2H, major rotamer), 3.02 (t, J=5.9 Hz, 2H, minor rotamer), 2.78 (s, 3H), 2.76 (t, J=6.7 Hz, 2H, minor rotamer), 2.67 (t, J=5.5 Hz, 2H, major rotamer), 2.32 (t, J=7.0 Hz, 2H, major rotamer); rotameric ratio is ~57:43 at 20° C.; MS (m/z) 279 [M+H]$^+$ ($^{35}$Cl).

Example 74

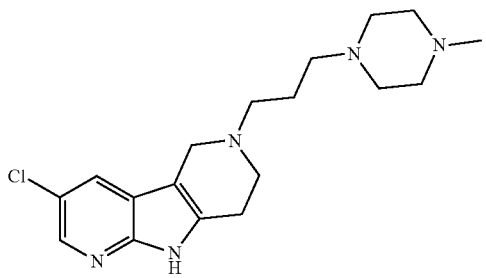 [SMILES: CN1CCN(CCCN2CCc3[nH]c4ncc(Cl)cc4c3C2)CC1]

Synthesis of: 3-Chloro-6-(3-morpholin-4-yl-propyl)-6,7,8,9-tetrahydro-5H-dipyrido[2,3-b;3',4'-d]pyrrole The title compound was obtained in 53% yield from intermediate 1.1 and 4-(3-chloropropyl)morpholine following the procedure described for example 1 (HPLC: 91%, RT: 2.18 min) $^1$H NMR (DMSO-d6) δ 11.56 (br s, 1H), 8.06 (d, J=2.6 Hz, 1H), 7.88 (d, J=2.6 Hz, 1H), 3.57 (t, J=4.4 Hz, 4H), 3.53 (s, 2H), 2.77 (s, 4H), 2.54 (t, J=7.0 Hz, 2H), 2.37-2.29 (m, 6H), 1.69 (quint., J=7.1 Hz, 2H); MS (m/z) 235 [M+H]$^+$ ($^{35}$Cl).

Example 75

Synthesis of: 3-Chloro-6-[3-(4-methyl-piperazin-1-yl)-propyl]-6,7,8,9-tetrahydro-5H-dipyrido[2,3-b;3',4'-d]pyrrole The title compound was obtained in 58% yield from intermediate 1.1 and 1-(3-chloropropyl)-4-methylpiperazine dihydrochloride following the procedure described for example 1 (HPLC: 93%, RT: 2.25 min) $^1$H NMR (DMSO-d6) δ 11.56 (br s, 1H), 8.06 (d, J=2.6 Hz, 1H), 7.88 (d, J=2.2 Hz, 1H), 3.53 (s, 2H), 2.77 (s, 4H), 2.30 (t, J=7.0 Hz, 6H), 2.55-2.50 (m, 6H), 2.14 (s, 3H), 1.68 (quint., J=7.0 Hz, 2H); MS (m/z) 248 [M+H]+ ($^{35}$Cl).

Example 76

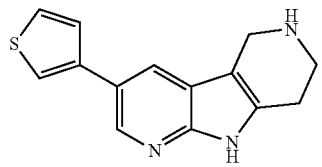 [SMILES: c1cc(-c2cnc3[nH]c4c(c3c2)CNCC4)cs1]

Synthesis of: 3-Thiophen-3-yl-6,7,8,9-tetrahydro-5H-dipyrido[2,3-b;3',4'-d]pyrrole A suspension of intermediate 1.1 (50 mg; 0.18 mmol), 3-thienylboronic acid (46 mg; 0.36 mmol), palladium(II) acetate (2 mg; 0.01 mmol), 2-dicyclohexylphosphino-2',6'-dimethoxybiphenyl (11 mg; 0.03 mmol) and potassium carbonate (99 mg; 0.71 mmol) in dioxane (2 mL) and water (0.2 mL) was placed in a microwave tube. The tube was sealed and the yellow suspension was heated at 100° C. overnight. The reaction mixture was cooled down and concentrated under vacuo. The residue was purified by chromatography on a Biotage KP-NH column with a Isolera system, using dichloromethane and methanol as eluents to afford the title compound (76 mg, 88%) as a white solid (HPLC: 99%, RT: 2.39 min). $^1$H NMR (DMSO-d6) δ 11.78 (br s, 1H), 9.13 (br s, 2H), 8.61 (d, J=2.2 Hz, 1H), 8.27 (d, J=2.2 Hz, 1H), 7.87 (dd, J=2.9, 1.5 Hz, 1H), 7.69 (dd, J=5.1, 2.9 Hz, 1H), 7.62 (dd, J=5.1, 1.5 Hz, 1H), 4.36 (s, 2H), 3.53 (br q, J=5.5 Hz, 2H), 3.04 (br t, J=5.7 Hz, 2H); MS (m/z) 256 [M+H]+.

Example 77

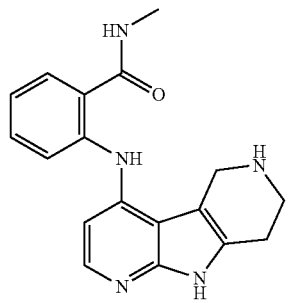 [SMILES: CNC(=O)c1ccccc1Nc1ccnc2[nH]c3c(c12)CNCC3]

Synthesis of: N-Methyl-2-(6,7,8,9-tetrahydro-5H-dipyrido[2,3-b;3',4'-d]pyrrol-4-ylamino)-benzamide Intermediate 77.1: 4-Chloro-6,7,8,9-tetrahydro-5H-dipyrido[2,3-b;3',4'-d]pyrrole To a solution of 4-cloro-5,7,8,9-tetrahydro-dipyrido[2,3-b;3',4'-d]pyrrole-6-carboxylic acid tert-butyl ester (1.00 g; 3.25 mmol) in methanol (50 mL) was added a solution of hydrogen chloride (16.25 ml; 2.00 M; 32.49 mmol) in diethyl ether. The yellow solution was stirred at room temperature overnight and a beige precipitate slowly formed. Ether (50 mL) was added and the yellow suspension was stirred for 15 min. The precipitate was filtered, washed with ether and dried under vacuo to afford the hydrochloride salt of intermediate 5.1 (877 mg, 96%) as a beige solid. $^1$H NMR (DMSO-d6) δ 12.21 (br s, 1H), 9.73 (br s, 2H), 8.15 (d, J=5.1 Hz, 1H), 7.20 (d, J=5.1 Hz, 1H), 4.46 (br s, 2H), 3.46 (br q, J=6.2 Hz, 2H), 3.07 (br t, J=5.9 Hz, 2H); MS (m/z) 208 [M+H]+ ($^{35}$Cl).

Example 77

N-Methyl-2-(6,7,8,9-tetrahydro-5H-dipyrido[2,3-b;3',4'-d]pyrrol-4-ylamino)-benzamide To a suspension of intermediate 5.1 (100 mg; 0.36 mmol), 2-amino-n-methylbenzamide (64 mg; 0.43 mmol) palladium (II) acetate (4 mg; 0.02 mmol), 2-dicyclohexylphosphino-2',4',6'-triisopropylbiphenyl (26 mg; 0.05 mmol), and potassium hydroxide (80 mg; 1.43 mmol) in tert-butanol (2 mL) was placed in a microwave tube. The tube was sealed and the yellow suspension was heated at 100° C. overnight. The reaction mixture was cooled down and concentrated under vacuo. The residue was purified by chromatography on a Biotage KP-NH column with a Isolera system, using dichloromethane and 1% ammonia in methanol as eluents to afford the title compound (34 mg, 28%) as a yellow solid (HPLC: 93%, RT: 3.97 min) $^1$H NMR (DMSO-d6) δ 11.13 (br s, 1H), 10.17 (br s, 1H), 8.66 (q, J=4.8 Hz, 1H), 7.85 (d, J=5.5 Hz, 1H), 7.68 (dd, J=8.1, 1.5 Hz, 1H), 7.56 (d, J=7.3 Hz, 1H), 7.43 (td, J=7.3, 1.5 Hz, 1H), 6.98 (t, J=8.1 Hz, 1H), 6.83 (d, J=5.5 Hz, 1H), 4.15 (s, 2H), 2.99 (br t, J=5.7 Hz, 2H), 2.78 (d, J=4.8 Hz, 1H), 2.63 (br t, J=5.1 Hz, 2H); MS (m/z) 322 [M+H]+.

Example 78

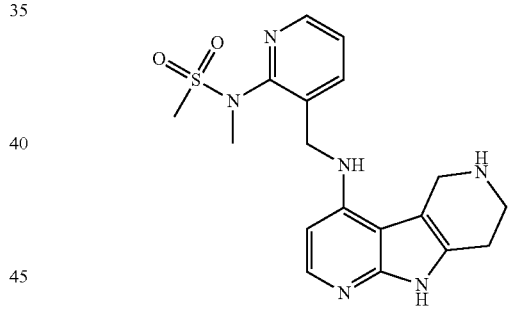

Synthesis of: N-Methyl-N-{3-[(6,7,8,9-tetrahydro-5H-dipyrido[2,3-b;3',4'-d]pyrrol-4-ylamino)-methyl]-pyridin-2-yl}-methanesulfonamide The title compound was obtained in 7% yield from intermediate 5.1 and N-(3-aminomethyl-pyridin-2-yl)-n-methyl-methanesulfonamide following the procedure described for example 5 (HPLC: 99%, RT: 2.13 min). $^1$H NMR (DMSO-d6) δ 9.39 (br s, 1H), 8.49 (dd, J=4.8, 1.8 Hz, 1H), 7.97 (d, J=7.0 Hz, 1H), 7.94 (t, J=6.6 Hz, 1H), 7.79 (dd, J=8.1, 1.8 Hz, 1H), 7.43 (dd, J=7.7, 4.8 Hz, 1H), 6.29 (d, J=7.3 Hz, 1H), 4.78 (d, J=5.9 Hz, 2H), 4.62 (s, 2H), 3.50 (br q, J=5.1 Hz, 2H), 3.28 (s, 3H), 3.18 (s, 3H), 3.03 (t, J=5.5 Hz, 2H), 2.63 (br t, J=5.1 Hz, 2H); MS (m/z) 387 [M+H]+.

VII. BIOLOGICA DATA

The susceptibility of a particular cell to treatment with the compounds according to the invention was determined by in vitro tests. Typically, a culture of the cell was combined with a compound according to the invention at various concentrations for a period of time that was sufficient to allow the active agents to induce cell death or to inhibit migration, usually between about one hour and one week. In vitro testing was carried out using cultivated cells from a biopsy sample. The viable cells remaining after the treatment then were counted.

Assays

The compounds of Formula I described in the examples were tested by the assays given below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

| Example Number | Src IC50 (nM)* |
|---|---|
| 15 | "++" |
| 58 | |
| 61 | |
| 62 | |
| 64 | |
| 67 | "+" |
| 69 | "+" |
| 70 | "+" |
| 71 | "+" |
| 68 | "+" | where "+" = 101-1,000 nM
"++" = 11-100 nM
"+++" = 1-10 nM

It is understood that in light of the teachings of this invention to one of ordinary skill in the art that certain changes and modifications may be made thereto without departing from the spirit and scope of the invention.

What is claimed is:

1. A compound according to Formula I

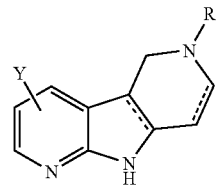

(I)

wherein:
R is H; halo; CN; NO$_2$; C$_1$-C$_6$ alkyl; CF$_3$; aryl; heteroaryl; aralkyl; alkaryl; heteroalkyl; carbocycle; C(=O)OR'; alkyl-C(=O)—; aryl-C(=O); —C(=O)aryl; —C(=O)heteroaryl; —C(=O)NH-aryl; —C(=O)NH-heteroaryl; aryl-C(=O)—; heteroaryl-C(=O); OR'; R'—SO$_2$—; SO$_2$—R'; SR'; R'—NH—C(=O)—; alkyl-O—C(=O)—; R'-alkyl-; R'—C(=O); or NR'R'; aryl-NH—C(=O)—; aryl-C(=O)—; OR'; R'—SO$_2$—; SO$_2$—R'; SR'; R'—NH—C(=O)—; alkyl-O—C(=O)—; R'-alkyl-; R'—C(=O); or NR'R';
R' is H; O; S; CONH2; alkyl; haloalkyl; alkylhalo; haloaryl; haloheteroaryl, cycloalkyl; aryl; heteroaryl; heteroalkyl; or heteroaryl;

Y is a) aryl-C(=O)—NH—NH-aryl-NH and aryl is phenyl, or b) Y is R'—NH or R';
-------- denotes the presence or absence of a double bond;
aryl, heteroaryl, heteroalkyl or cycloalkyl optionally may be substituted or unsubstituted, and may be a mono-, bi- or tricyclic ring structure in any combination of aryl, heteroaryl, heteroalkyl and/or cycloalkyl rings; and a pharmaceutically acceptable salt, tautomer and stereoisomer thereof, including mixtures thereof in all ratios.

2. A compound selected from the group consisting of:
N-[4-(6,7,8,9-Tetrahydro-5H-dipyrido[2,3-b;3',4'-d]pyrrol-4-ylamino)-phenyl]-benzamide;
N-[4-(6-Acetyl-6,7,8,9-tetrahydro-5H-dipyrido[2,3-b;3',4'-d]pyrrol-4-y amino)-phenyl]-benzamide;
Phenyl-(6,7,8,9-tetrahydro-5H-dipyrido[2,3-b;3',4'-d]pyrrol-4-yl)-amine;
Benzyl-(6,7,8,9-tetrahydro-5H-dipyrido[2,3-b;3',4'-d]pyrrol-4-yl)-amine;
(4-Fluoro-phenyl)-(6,7,8,9-tetrahydro-5H-dipyrido[2,3-b;3',4'-d]pyrrol-4-yl)-amine;
4-(4-Fluoro-phenyl)-6,7,8,9-tetrahydro-5H-dipyrido[2,3-b;3',4'-d]pyrrole;
(4-Fluoro-phenyl)-(4-phenylamino-5,7,8,9-tetrahydro-dipyrido[2,3-b;3',4'-d]pyrrol-6-yl)-methanone;
1-(4-Phenylamino-5,7,8,9-tetrahydro-dipyrido[2,3-b;3',4'-d]pyrrol-6-yl)-ethanone;
(3-Chloro-phenyl)-(4-phenylamino-5,7,8,9-tetrahydro-dipyrido[2,3-b;3',4'-d]pyrrol-6-yl)-methanone;
4-Phenylamino-5,7,8,9-tetrahydro-dipyrido[2,3-b;3',4'-d]pyrrole-6-carboxylic acid (3-chloro-phenyl)-amide;
[6-(3-Chloro-benzenesulfonyl)-6,7,8,9-tetrahydro-5H-dipyrido[2,3-b;3',4'-d]pyrrol-4-yl]-phenyl-amine;
N-{4-[6-(3-Chloro-benzoyl)-6,7,8,9-tetrahydro-5H-dipyrido[2,3-b;3',4'-d]pyrrol-4-ylamino]-phenyl}-benzamide;
N-Methyl-4-(6,7,8,9-tetrahydro-5H-dipyrido[2,3-b;3',4'-d]pyrrol-4-yl)-benzenesulfonamide;
4-(6-Acetyl-6,7,8,9-tetrahydro-5H-dipyrido[2,3-b;3',4'-d]pyrrol-4-yl)-N-methyl-benzenesulfonamide;
1-[4-(5-Chloro-benzo[1,3]dioxol-4-ylamino)-5,7,8,9-tetrahydro-dipyrido[2,3-b;3',4'-d]pyrrol-6-yl]-ethanone;
3-(3-Chloro-5,7,8,9-tetrahydro-dipyrido[2,3-h; 3',4'-d]pyrrol-6-ylmethyl)-benzonitrile;
3-Chloro-6-(3-methoxy-benzyl)-6,7,8,9-tetrahydro-5H-dipyrido[2,3-b;3',4'-d]pyrrole;
(4-Chloro-phenyl)-(3-chloro-5,7,8,9-tetrahydro-dipyrido[2,3-h; 3',4'-d]pyrrol-6-yl)-methanone.Hydrochloride Salt;
(3-Chloro-5,7,8,9-tetrahydro-dipyrido[2,3-b;3',4'-d]pyrrol-6-yl)-phenyl-methanone.Hydrochloride Salt;
(2-Chloro-phenyl)-(3-chloro-5,7,8,9-tetrahydro-dipyrido[2,3-b;3',4'-d]pyrrol-6-yl)-methanone.Hydrochloride Salt;
(3-Chloro-phenyl)-(3-chloro-5,7,8,9-tetrahydro-dipyrido[2,3-b;3',4'-d]pyrrol-6-yl)-methanone.Hydrochloride Salt;
4-(3-Chloro-5,7,8,9-tetrahydro-dipyrido[2,3-b;3',4'-d]pyrrole-6-carbonyl)-benzonitrile.Hydrochloride Salt;
3-(3-Chloro-5,7,8,9-tetrahydro-dipyrido[2,3-b;3',4'-d]pyrrole-6-carbonyl)-benzonitrile.Hydrochloride Salt;
(3-Chloro-5,7,8,9-tetrahydro-dipyrido[2,3-b;3',4'-d]pyrrol-6-yl)-(2-methoxy-phenyl)-methanone.Hydrochloride Salt;
(3-Chloro-5,7,8,9-tetrahydro-dipyrido[2,3-b;3',4'-d]pyrrol-6-yl)-(3-methoxy-phenyl)-methanone.Hydrochloride Salt;

(3-Chloro-5,7,8,9-tetrahydro-dipyrido[2,3-b;3',4'-d]pyrrol-6-yl)-(4-methoxy-phenyl)-methanone.Hydrochloride Salt;
3-Chloro-5,7,8,9-tetrahydro-dipyrido[2,3-b;3',4'-d]pyrrole-6-carboxylic acid (4-methoxy-phenyl)-amide.Hydrochloride Salt;
3-Chloro-5,7,8,9-tetrahydro-dipyrido[2,3-b;3',4'-d]pyrrole-6-carboxylic acid (4-cyano-phenyl)-amide.Hydrochloride Salt;
3-Chloro-5,7,8,9-tetrahydro-dipyrido[2,3-b;3',4'-d]pyrrole-6-carboxylic acid (4-chloro-phenyl)-amide.Hydrochloride Salt;
3-Chloro-5,7,8,9-tetrahydro-dipyrido[2,3-b;3',4'-d]pyrrole-6-carboxylic acid (3-methoxy-phenyl)-amide.Hydrochloride Salt;
3-Chloro-5,7,8,9-tetrahydro-dipyrido[2,3-b;3',4'-d]pyrrole-6-carboxylic acid (2-methoxy-phenyl)-amide.Hydrochloride Salt;
3-Chloro-5,7,8,9-tetrahydro-dipyrido[2,3-b;3',4'-d]pyrrole-6-carboxylic acid (3-chloro-phenyl)-amide.Hydrochloride Salt;
3-Chloro-6-(4-chloro-benzenesulfonyl)-6,7,8,9-tetrahydro-5H-dipyrido[2,3-b;3',4'-d]pyrrole;
3-Chloro-6-(2-chloro-benzenesulfonyl)-6,7,8,9-tetrahydro-5H-dipyrido[2,3-b;3',4'-d]pyrrole;
2-Chloro-6-(3-chloro-benzenesulfonyl)-6,7,8,9-tetrahydro-5H-dipyrido[2,3-b;3',4'-d]pyrrole;
3-Chloro-6-(2,5-dimethoxy-benzenesulfonyl)-6,7,8,9-tetrahydro-5H-dipyrido[2,3-b;3',4'-d]pyrrole;
3-Chloro-6-(2,4-dimethoxy-benzenesulfonyl)-6,7,8,9-tetrahydro-5H-dipyrido[2,3-b;3',4'-d]pyrrole;
3-Chloro-6-(3-methoxy-benzenesulfonyl)-6,7,8,9-tetrahydro-5H-dipyrido[2,3-b;3',4'-d]pyrrole;
3-Chloro-6-(4-methoxy-benzenesulfonyl)-6,7,8,9-tetrahydro-5H-dipyrido[2,3-b;3',4'-d]pyrrole;
3-(3-Chloro-5,7,8,9-tetrahydro-dipyrido[2,3-b;3',4'-d]pyrrole-6-sulfonyl)-benzonitrile;
4-(3-Chloro-5,7,8,9-tetrahydro-dipyrido[2,3-b;3',4'-d]pyrrole-6-sulfonyl)-benzonitrile;
3-Chloro-5,7,8,9-tetrahydro-dipyrido[2,3-b;3',4'-d]pyrrole-6-carboxylic acid (2-chloro-phenyl)-amide.Hydrochloride Salt;
3-(4-Phenoxy-phenylamino)-5,7,8,9-tetrahydro-dipyrido[2,3-b;3',4'-d]pyrrole-6-carboxylic acid tert-butyl ester;
3-(4-Methoxy-phenylamino)-5,7,8,9-tetrahydro-dipyrido[2,3-b;3',4'-d]pyrrole-6-carboxylic acid tert-butyl ester;
3-(2-Methoxy-phenylamino)-5,7,8,9-tetrahydro-dipyrido[2,3-b;3',4'-d]pyrrole-6-carboxylic acid tert-butyl ester;
3-(3-Methoxy-phenylamino)-5,7,8,9-tetrahydro-dipyrido[2,3-b;3',4'-d]pyrrole-6-carboxylic acid tert-butyl ester;
(4-Methoxy-phenyl)-(6,7,8,9-tetrahydro-5H-dipyrido[2,3-b;3',4'-d]pyrrol-4-yl)-amine;
(2-Methyl-3-trifluoromethyl-phenyl)-(6,7,8,9-tetrahydro-5H-dipyrido[2,3-b;3',4'-d]pyrrol-4-yl)-amine.bis-hydrochloride Salt;
(6,7,8,9-Tetrahydro-5H-dipyrido[2,3-b;3',4'-d]pyrrol-4-yl)-(3-trifluoromethyl-phenyl)-amine.Bishydrochloride Salt;
(3-Fluoro-4-methyl-phenyl)-(6,7,8,9-tetrahydro-5H-dipyrido[2,3-b;3',4'-d]pyrrol-4-yl)-amine.Bishydrochloride Salt;
(2-Methoxy-phenyl)-(6,7,8,9-tetrahydro-5H-dipyrido[2,3-b;3',4'-d]pyrrol-4-yl)-amine.Bishydrochloride Salt;
Pyridin-2-yl-(6,7,8,9-tetrahydro-5H-dipyrido[2,3-b;3',4'-d]pyrrol-4-yl)-amine.Bishydrochloride Salt;
(3-Fluoro-phenyl)-(6,7,8,9-tetrahydro-5H-dipyrido[2,3-b;3',4'-d]pyrrol-4-yl)-amine.Bishydrochloride Salt;
(4-Methyl-3-trifluoromethyl-phenyl)-(6,7,8,9-tetrahydro-5H-dipyrido[2,3-b;3',4'-d]pyrrol-4-yl)-amine.Bishydrochloride Salt;
Benzo[1,3]dioxol-5-yl-(6,7,8,9-tetrahydro-5H-dipyrido[2,3-b;3',4'-d]pyrrol-4-yl)-amine.Bishydrochloride Salt;
1-[4-(Benzo[1,3]dioxol-5-ylamino)-5,7,8,9-tetrahydro-dipyrido[2,3-b;3',4'-d]pyrrol-6-yl]-ethanone;
1-[4-(Naphthalen-1-ylamino)-5,7,8,9-tetrahydro-dipyrido[2,3-b;3',4'-d]pyrrol-6-yl]-ethanone;
1-[4-(3-Fluoro-4-methyl-phenylamino)-5,7,8,9-tetrahydro-dipyrido[2,3-b;3',4'-d]pyrrol-6-yl]-ethanone;
1-[4-(5,6,7,8-Tetrahydro-naphthalen-2-ylamino)-5,7,8,9-tetrahydro-dipyrido[2,3-b;3',4'-d]pyrrol-6-yl]-ethanone;
1-[4-(Naphthalen-2-ylamino)-5,7,8,9-tetrahydro-dipyrido[2,3-b;3',4'-d]pyrrol-6-yl]-ethanone;
1-[4-(3-Fluoro-phenylamino)-5,7,8,9-tetrahydro-dipyrido[2,3-b;3',4'-d]pyrrol-6-yl]-ethanone;
1-[4-(4-Fluoro-phenylamino)-5,7,8,9-tetrahydro-dipyrido[2,3-b;3',4'-d]pyrrol-6-yl]-ethanone;
1-[4-(3-Trifluoromethyl-phenylamino)-5,7,8,9-tetrahydro-dipyrido[2,3-b;3',4'd]pyrrol-6-yl]-ethanone;
1-[4-(Indan-5-ylamino)-5,7,8,9-tetrahydro-dipyrido[2,3-b;3',4'-d]pyrrol-6-yl]-ethanone;
[2-(3-Chloro-5,7,8,9-tetrahydro-dipyrido[2,3-b;3',4'-d]pyrrol-6-yl)-ethyl]-diethyl-amine.Hydrochloride Salt;
3-Chloro-6-(2-morpholin-4-yl-ethyl)-6,7,8,9-tetrahydro-5H-dipyrido[2,3-b;3',4'-d]pyrrole;
[4-(5-Chloro-benzo[1,3]dioxol-4-ylamino)-5,7,8,9-tetrahydro-dipyrido[2,3-b;3',4'-d]pyrrol-6-yl]-phenyl-methanone;
[4-(5-Chloro-benzo[1,3]dioxol-4-ylamino)-5,7,8,9-tetrahydro-dipyrido[2,3-b;3',4'-d]pyrrol-6-yl]-phenyl-methanone;
[4-(5-Chloro-benzo[1,3]dioxol-4-ylamino)-5,7,8,9-tetrahydro-dipyrido[2,3-b;3',4'-d]pyrrol-6-yl]-cyclopropyl-methanone;
[4-(5-Chloro-benzo[1,3]dioxol-4-ylamino)-5,7,8,9-tetrahydro-dipyrido[2,3-b;3',4'-d]pyrrol-6-yl]-cyclobutyl-methanone;
[4-(5-Chloro-benzo[1,3]dioxol-4-ylamino)-5,7,8,9-tetrahydro-dipyrido[2,3-b;3',4'-d]pyrrol-6-yl]-cyclopentyl-methanone;
[4-(5-Chloro-benzo[1,3]dioxol-4-ylamino)-5,7,8,9-tetrahydro-dipyrido[2,3-b;3',4'-d]pyrrol-6-yl]-cyclohexyl-methanone;
1-[4-(5-Chloro-benzo[1,3]dioxol-4-ylamino)-5,7,8,9-tetrahydro-dipyrido[2,3-b;3',4'-d]pyrrol-6-yl]-2-methyl-propan-1-one;
3-(3-Chloro-5,7,8,9-tetrahydro-dipyrido[2,3-b;3',4'-d]pyrrol-6-yl)-propionamide;
3-Chloro-6-(3-morpholin-4-yl-propyl)-6,7,8,9-tetrahydro-5H-dipyrido[2,3-b;3',4'-d]pyrrole;
3-Chloro-6-[3-(4-methyl-piperazin-1-yl)-propyl]-6,7,8,9-tetrahydro-5H-dipyrido[2,3-b;3',4'-d]pyrrole;
3-Thiophen-3-yl-6,7,8,9-tetrahydro-5H-dipyrido[2,3-b;3',4'-d]pyrrole; and
N-Methyl-2-(6,7,8,9-tetrahydro-5H-dipyrido[2,3-b;3',4'-d]pyrrol-4-ylamino)-benzamide.

3. A pharmaceutical composition or medicament comprising a compound of claim 1 or a pharmaceutically acceptable salt, tautomer or stereoisomer thereof, or any mixture thereof, and a pharmaceutically acceptable carrier, excipient, adjuvant and/or diluent.

4. A pharmaceutical composition or medicament comprising a compound of claim 2 or a pharmaceutically acceptable salt, tautomer or stereoisomer thereof, or any mixture thereof, and a pharmaceutically acceptable carrier, excipient, adjuvant and/or diluent.

5. A medicament comprising at least one compound of the general Formula I according to claim 1 and/or a pharmaceutically acceptable tautomer or stereoisomer thereof, including any mixture thereof, and at least one further medicament active agent.

6. A kit consisting of separate packs of:
   (a) an effective amount of a compound of claim 1 or a pharmaceutically acceptable salt, tautomer and stereoisomer thereof, including mixtures thereof in all ratios, and
   (b) an effective amount of a second medicament active ingredient.

* * * * *